United States Patent
Tsuzuki et al.

(10) Patent No.: US 8,157,936 B2
(45) Date of Patent: Apr. 17, 2012

(54) COMPOSITE CERAMIC GREEN SHEET, CERAMIC SINTERED BODY, GAS SENSOR DEVICE, GAS SENSOR, AND METHOD FOR MANUFACTURING COMPOSITE CERAMIC GREEN SHEET

(75) Inventors: Masashi Tsuzuki, Nagoya (JP); Shinya Awano, Kasugai (JP)

(73) Assignee: NGK Spark Plug Co., Ltd., Aichi (JP)

( * ) Notice: Subject to any disclaimer, the term of this patent is extended or adjusted under 35 U.S.C. 154(b) by 1186 days.

(21) Appl. No.: 11/066,182

(22) Filed: Feb. 25, 2005

(65) Prior Publication Data
US 2005/0189222 A1 Sep. 1, 2005

(30) Foreign Application Priority Data
Feb. 27, 2004 (JP) ............... P.2004-054136

(51) Int. Cl.
B28B 1/30 (2006.01)
G01N 27/406 (2006.01)
(52) U.S. Cl. .......... 156/89.12; 204/424; 428/60
(58) Field of Classification Search .......... 204/424; 428/58, 60, 212; 156/89.12
See application file for complete search history.

(56) References Cited

U.S. PATENT DOCUMENTS

| | | | | |
|---|---|---|---|---|
| 4,037,941 A * | 7/1977 | Belleson et al. | ........... | 359/218.1 |
| 4,698,192 A * | 10/1987 | Kuze et al. | ........... | 264/101 |
| 4,911,987 A * | 3/1990 | Sakata et al. | ........... | 428/469 |
| 5,292,693 A * | 3/1994 | Kaga et al. | ........... | 501/103 |
| 5,384,030 A | 1/1995 | Duce et al. | | |
| 5,756,215 A | 5/1998 | Sawamura et al. | | |
| 5,948,200 A * | 9/1999 | Nakazawa et al. | ........... | 156/248 |
| 6,572,747 B1 * | 6/2003 | Fouts et al. | ........... | 204/426 |
| 6,676,817 B2 * | 1/2004 | Noda et al. | ........... | 204/424 |
| 6,699,555 B2 * | 3/2004 | DiChiara, Jr. | ........... | 428/60 |
| 7,045,047 B2 * | 5/2006 | Nakae et al. | ........... | 204/425 |
| 2002/0108872 A1 * | 8/2002 | Symons et al. | ........... | 205/784 |
| 2003/0034247 A1 | 2/2003 | Noda et al. | | |

FOREIGN PATENT DOCUMENTS

| | | |
|---|---|---|
| JP | 62-227605 A | 10/1987 |
| JP | 6-305856 A | 11/1994 |
| JP | 7-237980 A | 9/1995 |
| JP | 07-237980 A | 9/1995 |
| JP | 7-299811 A | 11/1995 |
| JP | 2535617 B2 | 9/1996 |

* cited by examiner

*Primary Examiner* — Kaj K Olsen
(74) *Attorney, Agent, or Firm* — Sughrue Mion, PLLC

(57) ABSTRACT

A composite ceramic green sheet comprising: a first sheet portion comprising a first sheet material; a second sheet portion comprising a second sheet material, said second sheet portion differing in firing behavior from said first sheet portion; and a mixed portion provided between said first and second sheet portions, comprising a mixture of said first and second sheet materials, and having a width at least twice as large as a thickness of the composite ceramic green sheet, wherein said first and second sheet portions are integrated with each other thorough said mixed portion in a spread direction.

3 Claims, 14 Drawing Sheets

COMPOSITE CERAMIC GREEN SHEET, CERAMIC SINTERED BODY, GAS SENSOR DEVICE, GAS SENSOR, AND METHOD FOR MANUFACTURING COMPOSITE CERAMIC GREEN SHEET

FIELD OF THE INVENTION

The present invention relates to a ceramic green sheet having a plurality of sheet portions, a ceramic sintered body having a composite ceramic layer including a plurality of regions, a gas sensor device including a solid-electrolyte ceramic region and an insulating ceramic region, a gas sensor using the gas sensor device, and a method for manufacturing a composite ceramic green sheet.

BACKGROUND OF THE INVENTION

A composite ceramic green sheet which is a composite of at least two portions having different compositions has been hitherto known (see Japanese Patent No. 2535617 (Page 1 and FIG. 12)).

Japanese Patent No. 2535617 (Page 1 and FIG. 12) discloses, as one of manufacturing processes of ceramic green sheets, a technique for obtaining a composite ceramic green sheet by casting first and second slurries using a doctor blade method in the state where the first and second slurries are in contact with each other and in parallel to each other (see Claims 1 and FIG. 12).

SUMMARY OF THE INVENTION

There is a problem as follows, when a ceramic sintered body is produced using a composite ceramic green sheet manufactured in the technique disclosed in Japanese Patent No. 2535617 (Page 1 and FIG. 12). That is, it has been proved that when there is a difference in firing behavior between a first sheet portion and a second sheet portion, a ceramic sintered body after firing is formed as a ceramic sintered body in which a crack has been produced or a crack will be produced easily over or along a border between a first ceramic region obtained by sintering the first sheet portion and a second ceramic region obtained by sintering the second sheet portion. It has been believed that this is roughly because the first sheet portion and the second sheet portion are merely bonded to form an interface substantially perpendicular to the surface of the composite ceramic green sheet according to the technique disclosed in Japanese Patent No. 2535617 (Page 1 and FIG. 12).

Solid-electrolyte ceramic materials such as zirconia have ionic conductivity under a high temperature. Thus, the solid-electrolyte ceramic materials have been hitherto intended to be used as gas sensor devices such as members of fuel cells or NaS cells, oxygen sensors, etc.

In order to use such a solid-electrolyte ceramic material in a gas sensor device or the like, it is necessary to provide electrodes on the surfaces of the solid-electrolyte ceramic material so as to catch a difference in potential generated between the electrodes due to ion conduction. On the other hand, in order to lead wirings having electric continuity to the electrodes, it is preferable to use wirings formed by printing or the like on an insulator or particularly an insulating ceramic material such as alumina.

However, there is a difference in firing behavior between the solid-electrolyte ceramic material such as zirconia and the insulating ceramic material such as alumina when a green sheet is fired. For example, there is a difference in coefficient of thermal expansion. As a result, when a sheet portion made of the solid-electrolyte ceramic material and a sheet portion made of the insulating ceramic material are provided adjacently to each other in one green sheet, a crack may be produced over or along the both as described above.

Therefore, a gas sensor device or the like has been hitherto formed out of a lamination of green sheets formed separately, one green sheet being made of a solid-electrolyte ceramic material, the other green sheet being made of an insulating ceramic material.

However, when an electrode is formed on the surface (opposite to the insulating ceramic layer) of the solid-electrolyte ceramic layer, it is difficult to connect the electrode to a pad formed on the surface of the insulating ceramic layer laminated to the solid-electrolyte ceramic layer. That is, it is desired to connect the electrode to the pad on the insulating ceramic layer through a wiring layer formed for extracting the electrode onto the solid-electrolyte ceramic layer or through a via conductor penetrating the solid-electrolyte ceramic layer or a lateral conductor passing the lateral face thereof. However, the solid-electrolyte ceramic layer has ion conductivity in a high-temperature portion. Therefore, when the wiring layer or the via conductor is formed directly on the solid-electrolyte ceramic layer, the wiring layer or the via conductor is electrically connected to the electrode through the solid-electrolyte ceramic layer. For this reason, the wiring layer, the via conductor or the lateral conductor cannot be formed directly on the solid-electrolyte ceramic layer.

Therefore, an insulating ceramic coat of alumina or the like is applied to a predetermined region in the surface or back surface of the solid-electrolyte ceramic layer, and the wiring layer is formed on the insulating ceramic coat. Alternatively, the solid-electrolyte ceramic layer is made sufficiently large, and the via conductor or the lateral conductor is formed in a region whose temperature is low enough for the solid-electrolyte ceramic layer to have no ion conductivity (that is, to serve as an insulating ceramic layer). Thus, the electrode is connected to the wiring on the insulating ceramic layer by use of the wiring layer, the via conductor or the lateral conductor formed thus. Alternatively, an insulation layer such as an alumina layer is formed in the inner circumferential or lateral surface of a through hole, and a via conductor or a lateral conductor is formed to be insulated from the solid-electrolyte ceramic layer by the insulation layer. Thus, the electrode has to be connected to the wiring on the insulating ceramic layer by use of the insulation layer formed thus. However, in these techniques, there are some problems that there is an obstruction in making the product compact, or manufacturing is so troublesome that the cost increases.

In addition, according to the technique disclosed in Japanese Patent No. 2535617 (Page 1 and FIG. 12), when the first slurry and the second slurry are dried to form a green sheet, there may occur a difference in behavior such as a change in shrinkage rate or shrinkage ratio between the slurries (sheet portions) produced at the time of sheet formation, due to a difference in solvents included in the slurries, a difference in materials of ceramic powder included in the slurries, a difference in materials of binders, etc. In such a case, it has been proved that in a completed green sheet, there occurs a crack between the first sheet portion and the second sheet portion so that the green sheet cannot be used as a green sheet.

The present invention was developed in consideration of such problems. It is an object of the invention to provide a composite ceramic green sheet in which cracks hardly appear when a green ceramic material containing the composite ceramic green sheet is fired.

It is another object of the invention to provide a ceramic sintered body high in reliability without any crack or the like.

It is another object of the invention to provide a gas sensor device high in reliability without any crack or the like.

It is another object of the invention to provide a gas sensor using the gas sensor device high in reliability.

It is further another object of the invention to provide a method for manufacturing a composite ceramic green sheet with no crack.

In order to solve the foregoing problems, according to the first configuration of the invention, there is provided a composite ceramic green sheet comprising a first sheet portion comprising a first sheet material; a second sheet portion comprising a second sheet material, the second sheet portion differing in firing behavior from said first sheet portion; and a mixed portion provided between said first and second sheet portions, comprising a mixture of said first and second sheet materials, and having a width at least twice as large as a thickness of the composite ceramic green sheet, wherein said first and second sheet portions are integrated with each other thorough said mixed portion in a spread direction.

The composite ceramic green sheet according to the invention is formed into a single sheet comprising the first and second sheet portions different in firing behavior are adjacent to each other in the spread direction of the sheet. In addition, the first and second sheet portions are integrated with each other through a mixed portion made of a mixture of the first and second sheet materials, and having a width at least twice as large as the thickness of the sheet.

The composite ceramic green sheet may be shaped into a predetermined shape by punching, bending, winding or the like. Electrodes or the like may be formed in respective parts of the composite ceramic green sheet. Alternatively, the composite ceramic green sheet may be integrated with another ceramic green sheet or member by lamination or the like. After that, a green ceramic material made of the composite ceramic green sheet or a green ceramic material made of the composite ceramic green sheet integrated with another sheet or member may be fired. In such a case, it is possible to suppress a problem that a crack appears over or along an interface between ceramic portions corresponding to the first and second sheet portions in an obtained ceramic sintered body, or the ceramic sintered body is broken easily in this interface when stress is applied to the ceramic sintered body. Thus, it is possible to form a reliable ceramic sintered body.

Although the mixed portion is set so as to be made of a mixture of the first and second sheet materials and have a width at least twice as large as the thickness of the mixed region, the width may be made preferably three or more times, or more preferably five or more times as large as the thickness. This is because the difference in firing behavior between the first sheet portion and the second sheet portion can be absorbed over a wider width.

In this application, the spread direction means any direction perpendicular to the thickness direction of the ceramic green sheet (sheet portion). Accordingly, in the case of a flat plate-like green sheet, the spread direction means a planar direction along the surface thereof.

The sheet materials mean materials forming the sheet portions of the ceramic green sheet. Examples of the sheet materials include ceramic materials (ceramic powders), binders, additives such as porosifiers, residual water after drying slurries, alcohol, solvents such as organic solvents, etc.

Of them, specific examples of the ceramic materials include alumina, zirconia, metal oxide semiconductor ceramic (e.g. $TiO_2$ or $SnO_2$), etc.

Mixing the first and second sheet materials includes not only the case where the first and second sheet materials have been stirred and mixed so that the both cannot be distinguished from each other, but also the case where the both exist concurrently in a direction (thick direction) perpendicular to the green sheet surface in the state where the both can be distinguished from each other, for example, the case where the first and second sheet materials abut against each other with an interface crossing the thick direction obliquely, or the case where the first and second sheet materials are stirred and jigsawed, for example, like a marbling shape or a vortex shape so that the both can be distinguished from each other.

The firing behavior means behavior shown by each sheet portion when the composite ceramic green sheet is fired. For example, the behavior is provided in the form of the sintering start temperature or the firing shrinkage ratio of each ceramic material, the coefficient of thermal expansion of the ceramic material determining the thermal expansion quantity in a temperature drop period after sintering, the degreasing start temperature (binder decomposition temperature) in a debinder process, etc.

Further, examples of the sheet portions different in firing behavior include sheet portions different in behavior at the time of firing the sheet portions, such as the start time of firing shrinkage, the firing shrinkage quantity, the thermal shrinkage quantity in a temperature drop period after firing, or the like, due to a difference in sintering start temperature, firing shrinkage rate, thermal shrinkage quantity, or the like, caused by the difference in chemical composition of ceramic materials between the sheet portions. Specifically, one is a sheet portion of alumina ceramic, and the other is a sheet portion of zirconia ceramic. In addition, examples of the sheet portions may include sheet portions different in behavior at the time of firing the sheet portions due to the difference in particle size, specific surface area, chemical activity or the like between ceramic materials of the sheet portions even when the ceramic materials have one and the same composition. Specifically, both the sheet portions uses alumina ceramic having one and the same chemical composition as their ceramic materials, but one is a sheet portion made of alumina ceramic powder whose particle size is relatively large, while the other is a sheet portion made of alumina ceramic powder whose particle size is relatively small. Further, examples of the sheet portions may include sheet portions different in chemical composition as to binders, porosifiers such as carbon, caffeine, etc., or other additives used as the sheet portions together with the ceramic materials, or sheet portions different in composition ratio between a ceramic material and a binder or the like in each sheet portion. Specifically there is included the case where sheet portions are made of one and the same ceramic material but different from each other as to materials of binders contained in the sheet portions respectively, or the case where the composition ratio of the ceramic material in one sheet portion is relatively large, while that in the other sheet portion is relatively small. In addition, there is included the case where sheet portions are made of one and the same ceramic material but one sheet portion contains a porosifier so that the sheet portion will be formed into a porous ceramic material after firing, while the other sheet portion contains no porosifier so that the sheet portion will be formed into a dense ceramic material.

To this end, the following one is preferred as a composite ceramic green sheet using ceramic materials different in firing behavior. That is, it is preferable that the ceramic green sheet formed into a single sheet form in which a plurality of sheet portions are adjacent to each other in the spread direction is formed as a composite ceramic green sheet in which a first sheet portion made of a first ceramic material and a second sheet portion made of a second ceramic material different in firing behavior from the first ceramic material are adjacent to each other and integrated with each other through a mixing portion provided between the first sheet portion and the second sheet portion, made of a mixture of the first ceramic material and the second ceramic material, and having a width at least twice as large as the thickness of the sheet.

In such a manner, in spite of use of ceramic materials different in firing behavior, a reliable ceramic sintered body in which no crack or the like occurs after firing can be provided due to the mixed portion.

Further, according to a second configuration of the invention, the composite ceramic green sheet according to the aforementioned first configuration may be adapted so that a ratio of the first sheet material to the second sheet material contained in the mixed portion decreases from a side close to the first sheet portion to a side close to the second sheet portion, while a ratio of the second sheet material to the first sheet material contained in the mixed portion increases likewise.

With the composite ceramic green sheet configured thus, the firing behavior in the mixed portion changes gradually from the side close to the first sheet portion toward the side close to the second sheet portion. Accordingly, firing behavior does not change suddenly. When a ceramic sintered body is manufactured using the composite ceramic green sheet, cracks which might occur between a portion corresponding to one sheet portion and a portion corresponding to the other sheet portion hardly occur in the ceramic sintered body.

Specifically the following configuration is preferable. That is, the composite ceramic green sheet according to the second configuration is preferably adapted so that in the mixed portion, from the side close to the first sheet portion toward the side close to the second sheet portion, the thickness of the portion made of the first sheet material decreases while the thickness of the portion made of the second sheet material increases.

With the composite ceramic green sheet configured thus, a sudden change in firing behavior can be prevented surely. Accordingly, it is possible to surely prevent a problem that cracks occurs between a portion of the ceramic sintered body corresponding to one sheet portion and another portion corresponding to the other sheet portion.

According to a third configuration of the invention, the composite ceramic green sheet according to the first configuration may be adapted so that the first and second sheet materials are arranged in a jigsaw pattern within the mixed portion.

With the composite ceramic green sheet configured thus, the interface between the first sheet material and the second sheet material does not have a simple shape but has a complicated shape in which the first sheet material and the second sheet material abut against each other in the interface extending over a wide width. When a ceramic sintered body is manufactured using the composite ceramic green sheet, first and second ceramic materials obtained by firing the first and second sheet materials are coupled with each other complicatedly. Thus, cracks or the like hardly occur particularly in the ceramic sintered body.

Examples of forms in which the first sheet material and the second sheet material are jigsawed with each other include forms where there appears a pattern due to uneven mixture of the two kinds of sheet materials, for example, the form where the interface between the first sheet material and the second sheet material in the mixed portion is formed into an S-shape (zigzag shape) in section along the direction from the side close to the first sheet portion toward the side close to the second sheet portion and the thickness direction of the sheet, or the form where the first sheet material and the second sheet material appear as a marbling pattern or a vortex pattern.

According to a fourth configuration of the invention, the composite ceramic green sheet according to the first configuration may be adapted so that a first ceramic component present as a chief ceramic component (a ceramic component having the largest weight) in the first sheet material occupies a lower ratio among ceramic components in the mixed portion than in the first sheet portion, and a second ceramic component present as a chief ceramic component (a ceramic component having the largest weight) in the second sheet material and differing in firing behavior from the first ceramic component occupies a lower ratio among ceramic components in the mixed portion than in the second sheet portion.

In the composite ceramic green sheet according to the invention, the following relationship is established as to the ceramic components. That is, the ratio of the first ceramic component to the total of the ceramic components in the mixed portion is lower than that in the first sheet portion, while the ratio of the second ceramic component to the total of the ceramic components in the mixed portion is lower than that in the second sheet portion.

Accordingly, when the composite ceramic green sheet is fired, the mixed portion shows middle firing behavior between that of the first sheet portion and that of the second sheet portion. Thus, the composite ceramic green sheet is formed to relax the occurrence of stress caused by the difference in firing behavior between the first sheet portion and the second sheet portion so as to suppress the occurrence of cracks or the like.

Any ceramic component may be used as the second ceramic component if it is different in firing behavior from the first ceramic component. Accordingly, it will go well if the second ceramic component has different properties from the first ceramic component as to properties having influence on firing behavior. Specific examples of the second ceramic component include not only the case where the second ceramic component is different in firing behavior from the first ceramic component because the second ceramic component is made of a different composition (material) from that of the first ceramic component, but also the case where the second ceramic component is different in firing behavior from the first ceramic component because the second ceramic component has a different particle size, a different specific surface area, or the like, from that of the first ceramic component though the second ceramic component is made of the same material as the first ceramic component.

Further, according to a fifth configuration of the invention, the composite ceramic green sheet according to any one of the first to fourth configuration may be adapted so that at least one of the first and second sheet portions is colored so that the first and second sheet portions can be distinguished from each other.

When the first sheet portion corresponds to or resembles the second sheet portion in color tone in the composite ceramic green sheet in which the first sheet portion and the second sheet portion are adjacent to each other, it is difficult to know where the border between the first sheet portion and the second sheet portion is (where the mixed portion is) or which sheet portion each part belongs to at the time of handling. Thus, handling is apt to be difficult.

In contrast, in the green sheet according to the invention, the first sheet portion and the second sheet portion can be distinguished from each other by coloring. Accordingly, between the first and second sheet portions, it is easy to distinguish the sheet portions or the border (mixed portion) therebetween, so that it is easy to handle the green sheet.

Although both the first sheet portion and the second sheet portion may be colored individually, only one of the sheet portions may be colored so that it can be distinguished.

As for the method for coloring the sheet portion, for example, it can be considered that a paint is applied to the first sheet portion so as to color it after the green sheet is manufactured. It is, however, preferable that a dye or a pigment as a colorant is added to a slurry which will be formed into a sheet portion to be colored, so that the slurry itself is colored.

Further, as for the colorant, it is preferable to use an organic dye or the like, such as rhodamine, characterized in that the dye is evaporated or gasified due to heating or oxidation at the time of firing so that the dye does not survive in the fired ceramic layer. This is because the sheet portion can be distinguished by coloring while there is no fear that such a dye has influence on the characteristic of the fired ceramic layer.

According to a sixth configuration of the invention, the composite ceramic green sheet according to the fifth configuration may be adapted so that at least one of the first and second sheet materials is colored so that the first and second sheet materials can be distinguished from each other.

In such a manner, the first sheet portion and the second sheet portion can be distinguished from each other, while there is another advantage that the position of the mixed portion or the mixed condition of the first and second sheet materials in the mixed portion can be grasped easily.

Further, according to a seventh configuration of the invention, the composite ceramic green sheet according to any one of the first to sixth configurations may be adapted so that the first sheet portion is a solid-electrolyte ceramic sheet portion made of a solid-electrolyte ceramic material, and the second sheet portion is an insulating ceramic sheet portion made of an insulating ceramic material.

As described previously, a solid-electrolyte ceramic material obtained by sintering a solid-electrolyte ceramic material having zirconia as its chief component has ion conductivity under high temperature. It has been intended to use the solid-electrolyte ceramic material as a fuel cell, an NaS cell or a gas sensor device such as an oxygen sensor. In order to use a solid-electrolyte ceramic layer in a gas sensor device or the like, it is necessary to provide electrodes on the surfaces of the solid-electrolyte ceramic layer. On the other hand, in order to lead a wiring electrically connected to each electrode, it is preferable to use a wiring formed by printing or the like on insulating ceramic.

However, when a solid-electrolyte ceramic material is used, the solid-electrolyte ceramic material has ion conductivity. It is therefore difficult to lead a wiring in the planar direction or lead a wiring in the thickness direction of the solid-electrolyte ceramic material by use of a via conductor, a lateral wiring or the like in the form where the wiring is formed directly on the surface of the solid-electrolyte ceramic material. Accordingly, an insulating coat is applied onto any surface other than the surfaces where the electrodes are formed, and wirings are formed on the insulating coat. Alternatively, the solid-electrolyte ceramic layer is made large enough. As a result, there is a problem that it is difficult to miniaturize the ceramic sintered body including the solid-electrolyte ceramic material, or it is so troublesome to produce the via conductor or the like that the cost increases.

In contrast, in the composite ceramic green sheet according to the invention, the solid-electrolyte ceramic sheet portion and the insulating ceramic sheet portion are adjacent to each other through the mixed portion so as to form a single composite ceramic green sheet. Accordingly, by use of the composite ceramic green sheet, a wiring to be electrically connected to an electrode formed in the solid-electrolyte ceramic region (obtained by sintering the solid-electrolyte ceramic sheet portion) may be extracted to the surface of the insulating ceramic region (obtained by sintering the insulating ceramic portion) adjacent to the solid-electrolyte ceramic region. After that, the wiring can be led around without consideration of the ion conductivity of the solid-electrolyte ceramic region or the temperature thereof. Thus, it is possible to form a compact fuel cell, a compact gas sensor device, or the like, in which wirings can be led around easily.

Examples of the insulating ceramic material include ceramic materials such as alumina, mullite, silicon nitride, etc.

Examples of the solid-electrolyte ceramic material include zirconia etc.

Further, according to an eight configuration of the invention, a ceramic sintered body is obtained by firing a green ceramic material including a composite ceramic green sheet according to any one of the first to seventh configurations.

The ceramic sintered body according to the invention includes the aforementioned composite ceramic green sheet in a green ceramic material which has not yet been fired. Due to the mixed portion provided between the first sheet portion and the second sheet portion in the composite ceramic green sheet, cracks hardly occur due to firing. Accordingly, the ceramic sintered body obtained by firing a green ceramic material using the composite ceramic green sheet can be formed as a reliable ceramic sintered body having no crack or the like in the portion obtained by firing the composite ceramic green sheet.

According to a ninth configuration of the invention, a gas sensor device is obtained by firing a green gas sensor device material including the composite ceramic green sheet according to the seventh configuration. Of composite ceramic layers obtained by firing the composite ceramic green sheet, the solid-electrolyte ceramic sheet portion is formed into a solid-electrolyte ceramic region by firing. A surface electrode is provided on the surface of the solid-electrolyte ceramic region, and a back electrode is provided on the back surface of the solid-electrolyte ceramic region. The insulating ceramic sheet portion and the mixed portion are formed into an insulating ceramic region and a mixed region by firing the mixed portion. A surface wiring electrically connected to the surface electrode is provided on the surface of the insulating ceramic region and the mixed region. A back wiring electrically connected to the back electrode is provided on the back surface of the insulating ceramic region and the mixed region.

In the gas sensor device according to the invention, the composite ceramic green sheet according to the seventh configuration is included in a green gas sensor device material. In the composite ceramic layer obtained by firing the composite ceramic green sheet, the mixed region (portion obtained firing the mixed portion) is disposed between the solid-electrolyte ceramic region (portion obtained by firing the solid-electrolyte ceramic sheet portion) and the insulating ceramic region (portion obtained by firing the insulating ceramic a sheet portion). Accordingly, cracks hardly occur between the solid-electrolyte ceramic region and the insulating ceramic region due to firing. Thus, it is possible to obtain a reliable gas sensor device having no crack between the solid-electrolyte ceramic region and the insulating ceramic region.

Further, in the gas sensor device, the solid-electrolyte ceramic region, the insulating ceramic region and the mixed region are formed as a single composite ceramic layer. The surface electrode and the back electrode formed on the solid-electrolyte ceramic region are extracted using the surface wiring and the back wiring to the surface and back surface of the insulating ceramic region adjacent to the solid-electrolyte ceramic region through the surface and back surface of the mixed region respectively. Accordingly, it is not necessary to make the solid-electrolyte ceramic region larger than necessary, or to form a complicated via conductor or the like, such as a via conductor or a lateral conductor insulated from the solid-electrolyte ceramic layer. Thus, the gas sensor device becomes compact and simple in wiring configuration.

Further, according to a tenth configuration of the invention, a gas sensor includes a gas sensor device according to the ninth configuration adapted for detecting the specific gas.

In the gas sensor according to the invention, due to use of the aforementioned gas sensor device, it is possible to obtain a compact and reliable gas sensor.

In order to solve the foregoing problems, according to an eleventh configuration of the invention, a ceramic sintered body includes one or plural ceramic layers. At least one of the ceramic layers is a single composite ceramic layer including a first region comprising a first ceramic material, a second region comprising a second ceramic material differing in firing behavior from the first ceramic material, and a mixed region provided between the first and second regions, comprising a mixture of the first and second ceramic materials, and having a width at least twice as large as thickness thereof. The first region, the mixed region and the second region are integrated with one another in a spread direction of the ceramic layers.

In the ceramic sintered body according to the invention, one of ceramic layers belonging to the ceramic sintered body is a composite ceramic layer including a mixed region between a first region and a second region. The mixed region is made of a mixture of a first ceramic material and a second ceramic material and has a width two or more times as large as the thickness of the layer. Accordingly, though the first region and the second region are made ceramic materials different in firing behavior, the difference in firing behavior is relaxed due to the mixed region between the first and second regions. Thus, cracks hardly occur on and after firing. It is therefore possible to obtain a reliable ceramic sintered body in which cracks are absent or hardly occur in the composite ceramic layer.

It will go well if the first and second ceramic materials are different in firing behavior. The first and second ceramic materials are typically different in chemical composition (for example, zirconia and alumina). However, the first and second ceramic materials may belong to one and the same kind (for example, both alumina) if they are different in firing behavior due to a difference in particle size, porosity or the like.

Further, the ceramic sintered body may be modified as follows. That is, the ceramic sintered body according to the eleventh configuration is preferably adapted so that the mixed region is designed so that the ratio of the first ceramic material contained in the mixed portion decreases from the side close to the first region to the side close to the second region, while the ratio of the second ceramic material contained in the mixed portion increases likewise. According to this ceramic sintered body, the difference in firing behavior at the time of firing is relaxed gradually due to the existence of the mixed region. Thus, it is possible to securely obtain a reliable ceramic sintered body in which there is no crack or cracks hardly occur.

Further, the ceramic sintered body is preferably modified as follows. That is, the mixed region is designed so that the thickness of the portion made of the first ceramic material decreases from the side close to the first region to the side close to the second region, while the thickness of the portion made of the second ceramic material increases likewise. According to this ceramic sintered body, it is possible to securely obtain a more reliable ceramic sintered body in which there is no crack or cracks hardly occur.

Alternatively, the ceramic sintered body according to the eleventh configuration is preferably adapted so that the first ceramic material and the second ceramic material is jigsawed with each other in the mixed region. With the ceramic sintered body configured thus, the interface between the first ceramic material and the second ceramic material is not formed into a simple shape but the both abut against each other in the interface having a complicated shape. Thus, cracks hardly occur in the ceramic sintered body.

Further, according to a twelfth configuration of the invention, the ceramic sintered body according to the eleventh configuration may include a first ceramic layer comprising the first ceramic material, and the aforementioned composite ceramic layer laminated to the first ceramic layer and sintered integrally therewith. In a portion of the mixed region of the composite ceramic layer abutting against the first ceramic layer, the first ceramic material abuts against the first ceramic layer over a wider area than the second ceramic material.

In such a manner, stress generated by the difference in firing behavior between the first ceramic layer and the composite ceramic layer or particularly between the first ceramic layer and the mixed region of the composite ceramic layer can be reduced so that cracks generated by the stress can be also suppressed.

In order to solve the foregoing problems, according to a thirteenth configuration of the invention, a gas sensor device includes one or plural ceramic layers. At least one of the ceramic layers is a composite ceramic layer including a solid-electrolyte ceramic region comprising a solid-electrolyte ceramic material, an insulating ceramic region made of an insulating ceramic material differing in firing behavior from the solid-electrolyte ceramic material, and a mixed region provided between the solid-electrolyte ceramic region and the insulating ceramic region, comprising a mixture of the solid-electrolyte ceramic material and the insulating ceramic material, and having a width at least twice as large as a thickness thereof. The solid-electrolyte ceramic region, the mixed region and the insulating ceramic region are integrated with one another in a spread direction of the ceramic layers. Of the composite ceramic layer, the solid-electrolyte ceramic region has a surface electrode on its surface, and a back electrode on its back surface. A surface wiring electrically connected to the surface electrode is provided on the surface of the insulating ceramic region and the mixed region of the composite ceramic layer, while a back wiring electrically connected to the back electrode is provided on the back surface of the insulating ceramic region and the mixed region.

In the gas sensor device according to the invention, at least one of the ceramic layers is a composite ceramic layer having a mixed region between a solid-electrolyte ceramic region and an insulating ceramic region. Accordingly, in the composite ceramic layer, cracks hardly occur on and after firing due to the difference in firing behavior between a solid-electrolyte ceramic material and an insulating ceramic material. It is therefore possible to obtain a reliable gas sensor device in which there is no crack in the composite ceramic layer.

Further, in at least one of the ceramic layers, a solid-electrolyte ceramic region, an insulating ceramic region and a mixed region are formed into a single composite ceramic layer. A surface electrode and a back electrode are provided on the solid-electrolyte ceramic region, and a surface wiring and a back wiring electrically connected to the electrodes are provided on the mixed region and the insulating ceramic region. Accordingly, it is not necessary to make the solid-electrolyte ceramic region larger than necessary, or to form a complicated via conductor or the like, such as a via conductor or a lateral conductor insulated from the solid-electrolyte ceramic layer. Thus, the gas sensor device becomes compact and simple in wiring configuration.

The solid-electrolyte ceramic material and the insulating ceramic material are different in firing behavior due to the difference in sintering start temperature, sintering shrinkage ratio, coefficient of thermal expansion, etc. between the both.

Further, the gas sensor device is preferably modified as follows. That is, the mixed region is designed so that the ratio of the solid-electrolyte ceramic material contained in the mixed portion decreases from the side close to the solid-electrolyte ceramic region to the side close to the insulating ceramic region, while the ratio of the insulating ceramic material contained in the mixed portion increases likewise.

Further, the mixed region is preferably designed so that the thickness of the portion made of the solid-electrolyte ceramic material decreases from the side close to the solid-electrolyte ceramic region to the side close to the insulating ceramic region, while the thickness or the portion made of the insulating ceramic material increases likewise.

Alternatively, the mixed region is preferably designed so that the solid-electrolyte ceramic material and the insulating ceramic material are jigsawed with each other. In these modified gas sensor devices, cracks hardly occur.

Further, according to a fourteenth configuration of the invention, the gas sensor device according to the thirteen configuration may be adapted so that an insulating ceramic layer comprising the insulating ceramic material, and the aforementioned composite ceramic layer laminated to the insulating ceramic layer and sintered integrally therewith are provided, while in a portion of the mixed region of the composite ceramic layer abutting against the insulating ceramic layer, the insulating ceramic material abuts against the insulating ceramic layer over a wider area than the solid-electrolyte ceramic material.

In such a manner, stress caused by the difference in firing behavior between the insulating ceramic layer and the composite ceramic layer or particularly between the insulating ceramic layer and the mixed region of the composite ceramic layer can be reduced. Thus, cracks which might occur due to such stress can be also suppressed.

Further, according to a fifteen configuration of the invention, the gas sensor device according to the fourteenth configuration may be adapted to further comprises a heater wiring through which current is passed for heating the solid-electrolyte ceramic region, wherein the insulating ceramic layer electrically insulates the composite ceramic layer from the heater wiring.

When the gas sensor device has a heater wiring, a current flowing in the heater wiring may leak through the insulating ceramic layer. The leakage current may have influence on the sensor output generated between the surface electrode and the back electrode on the solid-electrolyte ceramic region. Thus, there is a fear that a proper output cannot be obtained.

In contrast, in the gas sensor device according to the invention, in the mixed region of the composite ceramic layer, the area where the insulating ceramic material abuts against the insulating ceramic layer is made larger than the area where the solid-electrolyte ceramic material abuts against the insulating ceramic layer. In accordance therewith, a leakage current hardly occurs, so that the influence of the leakage current can be reduced.

Further, according to a sixteenth configuration of the invention, a gas sensor including a gas sensor device according to any one of the thirteenth to fifteen configurations adapted for detecting specific the specific gas.

Since the gas sensor uses the aforementioned gas sensor device, the gas sensor can be made compact in size and low in cost.

In order to solve the foregoing problems, according to a seventeenth configuration of the invention, a method for manufacturing a composite ceramic green sheet constituting a single sheet and having a plurality of sheet portions adjacent one another in stripe form is provided. The method includes: applying a first slurry onto a web and a second slurry onto the web at a distance from the first slurry in a widthwise direction, the first slurry containing a first sheet material, and the second slurry containing a second sheet material having a different sheet forming behavior from the first slurry; and expanding the first slurry on the web toward the second slurry in the widthwise direction, and expanding the second slurry on the web toward the first slurry in the widthwise direction, so as to form a slurry mixed portion in which the first slurry and the second slurry are mixed on the web, wherein a first sheet portion made of the first sheet material and a second sheet portion made of the second sheet material are integrated with each other through a mixed portion provided between the first sheet portion and the second sheet portion in which the first sheet material and the second sheet material are mixed.

First, consider the case where there is a difference in sheet forming behavior between the first slurry and the second slurry. In this case, when the first slurry and the second slurry are cast in parallel at one time so as to be formed into a ceramic green sheet in which the first sheet portion and the second sheet portion are formed like stripes, the following problem is apt to occur. That is, when the first and second slurries are formed into a sheet by drying, there is a difference in behavior in sheet formation, such as degrees in shrinkage due to evaporation of solvents or the like. Thus, there may occur a crack in the interface between the first sheet portion and the second sheet portion in the completed green sheet.

In contrast, in the manufacturing method according to the invention, the first and second slurries applied onto the web are regulated by a blade edge of a regulating member such as a doctor blade. Thus, the first and second slurries are expanded in the widthwise direction of the web till the application thickness thereof is regulated. A slurry mixed portion is formed in such a manner.

As a result, in spite of a difference in sheet forming behavior between the first and second slurries when they are dried and formed into a sheet, the difference in behavior such as degrees in shrinkage is relaxed by the slurry mixed portion. Thus, cracks are prevented from occurring in the interface between the first sheet portion and the second sheet portion in the completed green sheet.

A mixed portion obtained by drying the slurry mixed portion is formed in the composite ceramic green sheet according to the invention. When the composite ceramic green sheet is fired in spite of a difference in firing behavior between the first sheet material and the second sheet material, cracks which may occur near the border between the first sheet portion and the second sheet portion due to the difference in firing behavior can be prevented effectively due to the existence of the mixed portion.

The sheet forming behavior means the behavior occurring in a slurry when the slurry (green sheet) is shrunk due to evaporation of a solvent contained in the slurry till the slurry applied onto a web is dried and formed into a green sheet.

The difference in sheet forming behavior means the difference in sheet forming behavior between two slurries to be compared with each other. For example, the difference in sheet forming behavior such as a shrinkage rate or a change in shrinkage ratio may be caused by a difference in heat of evaporation, evaporating temperature or evaporation rate between solvents (water, alcohol, organic solvents, etc.) contained in the slurries, a difference in material, particle size or specific surface area between ceramic powders contained in the slurries, a difference in material between binders contained in the slurries. For example, when one of the slurries is dried more quickly, the slurry shrinks earlier. In addition, the difference in behavior may be caused by a difference in composition ratio of contained solvent, ceramic powder and binder between the slurries.

Figure 1:
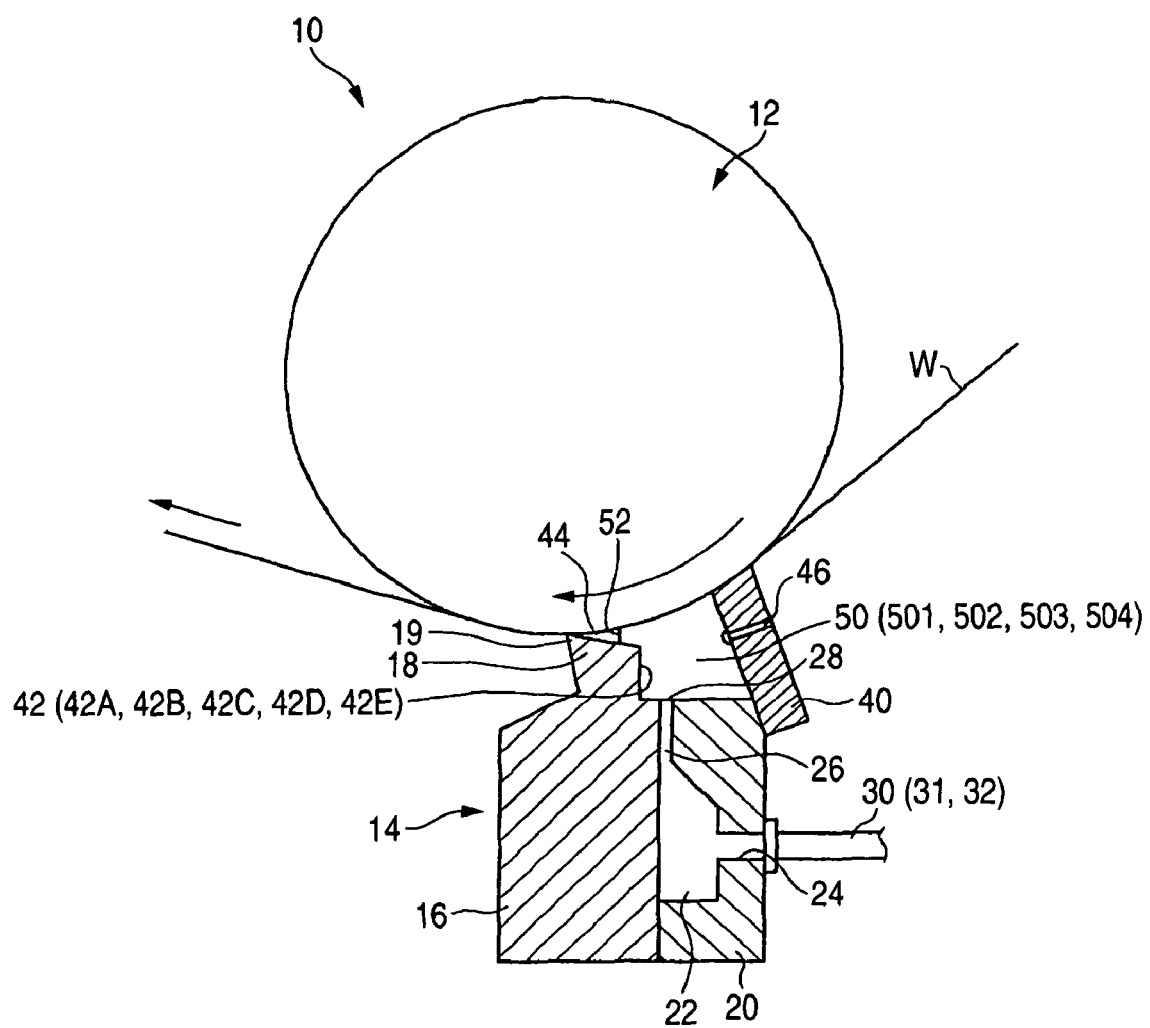
FIG. 1 is an explanatory view showing a structure of a main portion of sheet manufacturing apparatus (lip coater) used for manufacturing of a composite ceramic green sheet according to Embodiment 1, which view shows a section taken in a direction (web longitudinal direction) perpendicular to the axis of a roller.

DESCRIPTION OF REFERENCE NUMERALS AND SIGNS 10 sheet manufacturing apparatus (lip coater)
16 head body
18 doctor edge portion
19 edge
20 cover
22 first reservoir chamber
28, 28A, 28B, 28C, 28D, 28E slurry outlet
42, 42A, 42B, 42C, 42D, 42E second reservoir chamber
44, 441, 442, 443 mixed space
50, 501, 502, 503, 504, 150 partition member
52, 521, 522, 523, 524, 152 front end surface (of partition member)
W web
1 first slurry
2 second slurry
3 first sheet material
4 second sheet material
5 alumina ceramic material
6 zirconia solid-electrolyte ceramic material
7 dense alumina ceramic material
8 porous alumina ceramic material
CG, CG1, CG2, CG3 composite ceramic green sheet
BS, CS interface
SL separation section
SN mixing section
R1, R11, R12, R13 alumina sheet portion (first sheet portion, insulating ceramic sheet portion)
R2, R21, R22 zirconia sheet portion (second sheet portion, solid-electrolyte ceramic sheet portion)
RM, RM1, RM2, RM3, RM4 mixed portion
ST1, ST2, ST3 sheet thickness
SMW1, SMW2, SMW3 mixed width
GS, 100, 200, 400 gas sensor device (ceramic sintered body)
FC1, FC2, FC3, 101, 111, 201, 211, 401 composite ceramic layer
C1 alumina region (first ceramic region, insulating ceramic region)
C2 zirconia region (second ceramic region, solid-electrolyte ceramic region)
CM mixed region
CA1 dense alumina region (first ceramic region)
CA2 porous alumina region (second ceramic region)
CAM mixed region (of dense alumina and porous alumina)
106, 206, 236, 406 through hole
221, 231 alumina layer
121, 122, 124, 241, 242, 251 electrode layer
121A, 241A electrode portion (surface electrode)
124A, 251A electrode portion (back electrode)
121B, 241B pad portion (surface wiring)
124B, 251B pad portion (back wiring)
121C, 241C wiring portion (surface wiring)
124C, 251C wiring portion (back wiring)
123, 223, 237, 423 via conductor
280, 480 gas sensor device portion
290 heater portion
300 gas sensor
311 metal shell
341 protector
351 metal outer casing
357 caulked portion
361 lead
371 terminal unit
372 metal terminal
373 separator
381 grommet

DETAILED DESCRIPTION OF THE INVENTION

Embodiment 1

A first embodiment of the invention will be described with reference to FIGS. 1-6. First, description will be made about manufacturing of a composite ceramic green sheet CG according to the invention. In this embodiment, description will be made about the case where lip coater type sheet manufacturing apparatus 10 described with reference to FIGS. 1-4 is used for manufacturing of a composite ceramic green sheet CG1. The sheet manufacturing apparatus 10 applies a first slurry 1 and a second slurry 2 like stripes on one surface (lower surface in FIG. 1) of a long belt-like web W fed by rotation of a roller 12 in a direction (clockwise) showing by the arrows in FIG. 1, and dries the applied first and second slurries 1 and 2. Thus, a composite ceramic green sheet CG (CG1) is manufactured.

Slurries having compositions shown in Table 1 were used as the first and second slurries 1 and 2. That is, the first slurry 1 contains an alumina ceramic material added with a small amount of zirconia, as its ceramic material. On the other hand, the second slurry 2 contains a zirconia solid-electrolyte ceramic material having zirconia as its main component and added with 20 wt % of alumina, as its ceramic material.

The first slurry 1 looks pink due to an extremely small amount of red rhodamine added thereto as a colorant. On the other hand, the second slurry 2 looks white. The rhodamine is decomposed, fired and gasified when a composite ceramic layer which will be described later is sintered. Therefore, the rhodamine does not survive in an alumina ceramic region after sintering.

TABLE 1

| prepared raw materials | first slurry | second slurry |
|---|---|---|
| alumina powder | 97.0 | 20.0 |
| zirconia (containing $Y_2O_3$) powder | 3.0 | 80.0 |
| urethane resin water-based emulsion | 20.0 | 15.0 |
| Plasticizer | 2.0 | 1.0 |
| Dispersant | 0.2 | 0.2 |
| colorant (rhodamine) | $10^{-4}$ | — |
| Antifoamer | 0.2 | 0.2 |
| Water | 56.0 | 37.5 | per 100 parts by weight of ceramic component

Of the sheet manufacturing apparatus 10, a nozzle head 14 for applying the first and second slurries 1 and 2 onto the web W has a head body 16, a cover 20 and a wall member 40. The cover 20 is disposed on the upstream side (right side in FIG. 1) of the head body 16 so as to form a first reservoir chamber 22 between the cover 20 and the head body 16. The wall member 40 is provided between the cover 20 and the web W so as to form a second reservoir chamber 42 on the upstream side (right side in FIG. 1) of a doctor edge portion 18 of the head body 16. In the head body 16, the distance between an edge 19 at the edge of the doctor edge portion 18 and the web W is adjusted so that the application thickness (that is, sheet thickness after drying) of each slurry (first or second slurry) applied to the web W can be adjusted.

A slurry pressure-pumped through a tube 30 is injected into the first reservoir chamber 22 through a slurry injection path 24. Further, the injected slurry passes through a slurry outlet path 26, and is injected into the second reservoir chamber 42 through a slurry outlet 28 and introduced to the edge 19.

The pressure applied to the slurry is measured by a pressure sensor 46 attached to the wall member 40. The pressure is controlled to be constant, so that the application thickness of the slurry is made constant.

Figure 2:
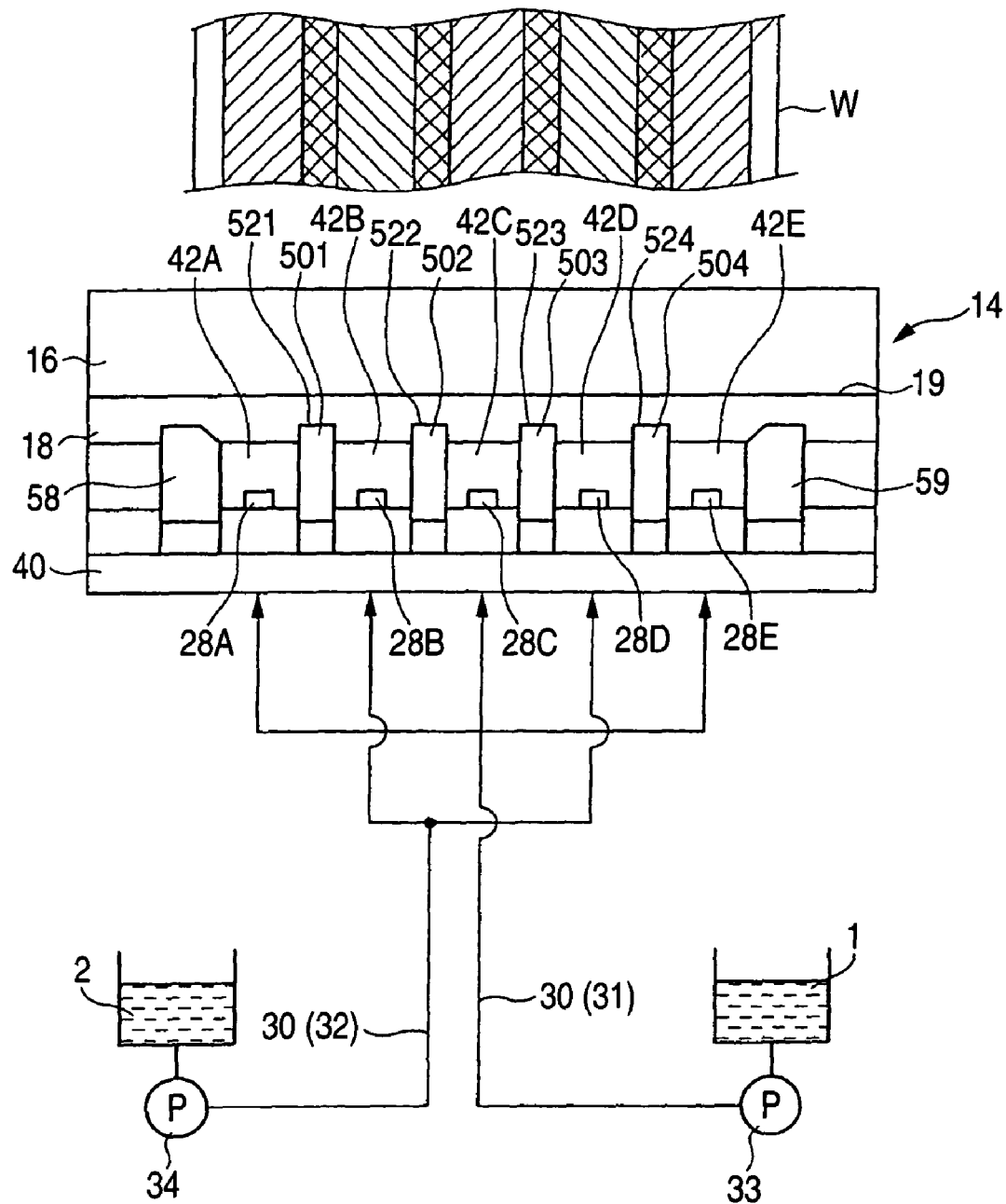
FIG. 2 is an explanatory view showing the structure of the main portion of the sheet manufacturing apparatus (lip coater) depicted in FIG. 1, which view shows a section taken in a direction (web widthwise direction) parallel to the axis of the roller.
Figure 5:
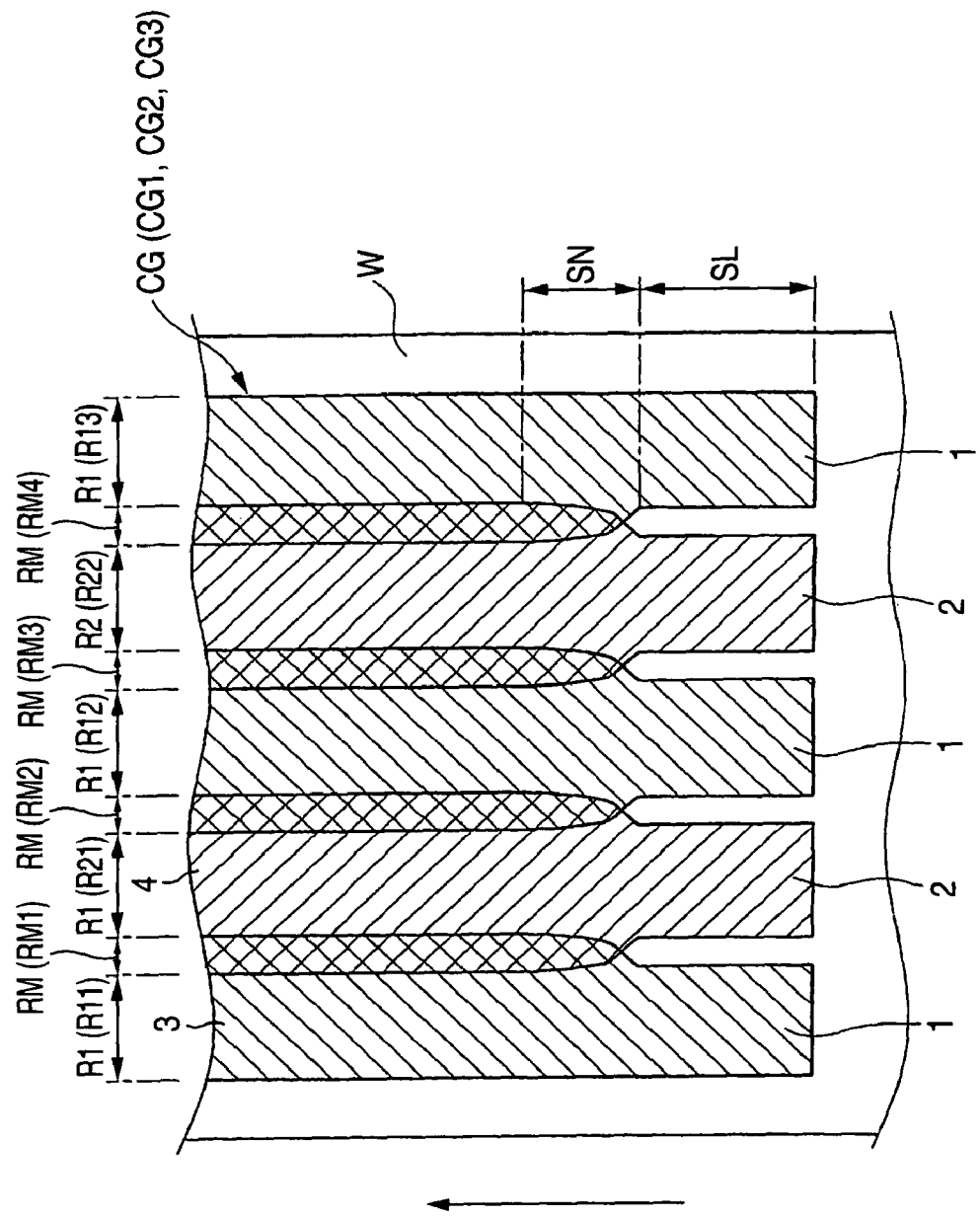
FIG. 5 is an explanatory view showing a form of a composite ceramic green sheet (slurries) formed on a web.

As for the number of each of the first and second reservoir chambers 22 and 42, one may be sufficient in normal sheet manufacturing apparatus. However, in Embodiment 1, as shown in FIG. 5, a striped composite ceramic green sheet CG1 in which the first slurry 1 and the second slurry 2 are arranged alternately is manufactured. To this end, in the sheet manufacturing apparatus 10, four partition members 50 (501, 502, 503 and 504) are disposed at intervals in the widthwise direction (left/right direction in FIG. 2 or direction perpendicular to the paper in FIG. 1) of the web W in addition to the side wall members 58 and 59 (see FIG. 2) for defining the total width of the ceramic green sheet. Accordingly, the second reservoir chamber 42 is partitioned into five chambers. On the other hand, though there is no specific illustration about the first reservoir charter 22, the first reservoir chamber 22 is also partitioned into five chambers by the cover 20. In the second reservoir chamber 42, as shown in FIG. 2, five second reservoir chambers 42A, 42B, 42C, 42D and 42E are formed. In addition, slurry outlets 28A, 28B, 28C, 28D and 28E are opened to the second reservoir chambers 42A and so on respectively.

In addition, as shown in FIG. 2, a first tube 31 into which the first slurry 1 is sent by a pressure pump 33 branches into three. On the other hand, a second tube 32 into which the second slurry 2 is sent by a pressure pump 34 branches into two. These branches of the tubes 31 and 32 are disposed alternately so that the first slurry 1 is injected into the second reservoir chambers 42A, 42C and 42E of the five second reservoir chambers through the first reservoir chambers, while the second slurry 2 is injected into the second reservoir chambers 42B and 42D likewise. That is, the second reservoir chambers 42A, 42C and 42E filled with the first slurry 1 and the second reservoir chambers 42B and 42D filled with the second slurry 2 are disposed alternately.

Figure 3:
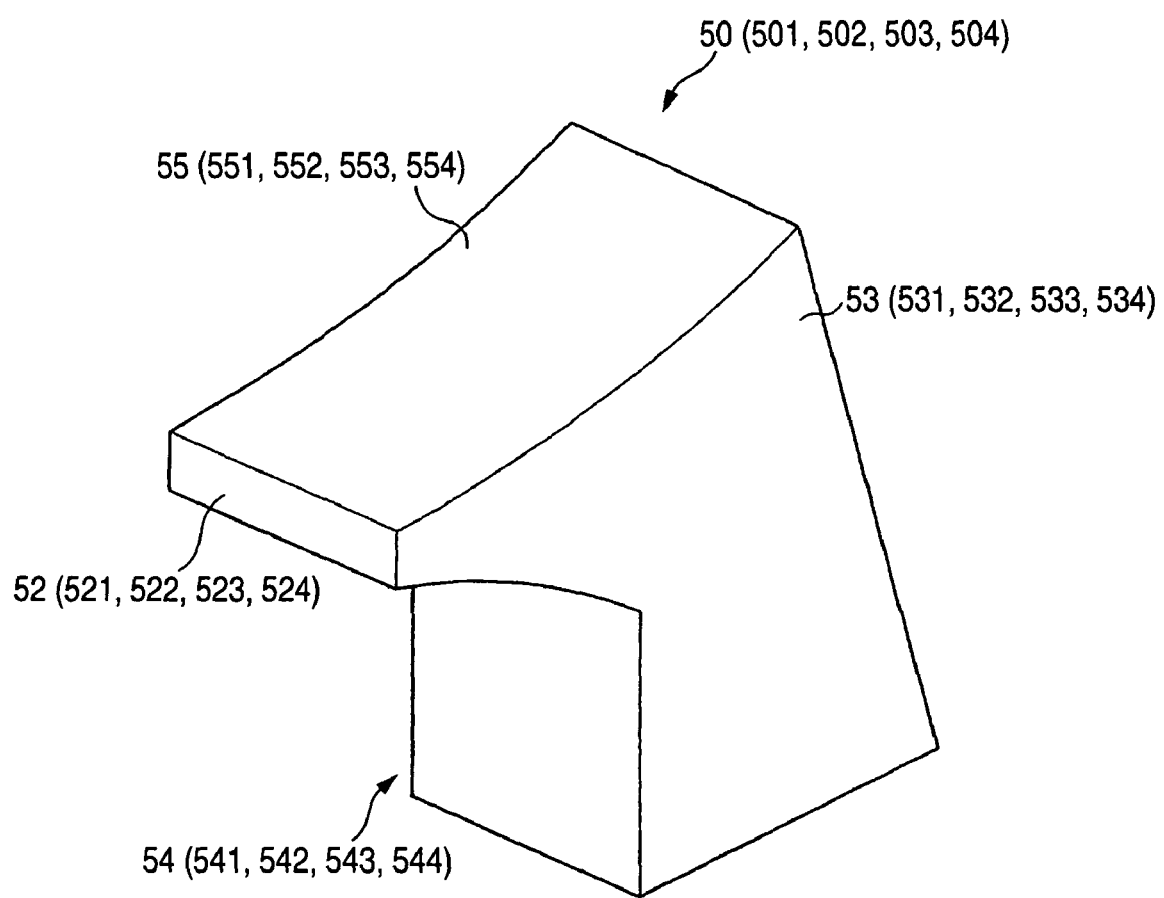
FIG. 3 is an explanatory view showing a shape of a partition member for use in the sheet manufacturing apparatus (lip coater) in FIG. 1.

As shown in FIG. 3, each partition member 50 (501, 502, 503, 504) has a web opposed surface 55 (551, 552, 553, 554), a first side surface 53 (531, 532, 533, 534) and a second side surface 54 (541, 542, 543, 544). The web opposed surface 55 is opposed to the web W in contact therewith or at a slight distance therefrom. The first and second side surfaces 53 and 54 face in the widthwise direction (left/right direction in FIG. 2) of the web W. Further, on the downstream side (left lower side in FIG. 3 or upper side in FIG. 2) of the web opposed surface 55, the partition member 50 has a front end surface 52 (521, 522, 523, 524) meeting the web opposed surface 55 at right angles. With reference to FIG. 1, the front end surface 52 is located on the upstream side (left side in FIG. 1 or lower side in FIG. 2) of the edge 19 of the doctor edge portion 18 in order to make it understood easily.

Accordingly, a mixing space 44 where there is no partition member in the widthwise direction of the web W is formed between the front end surface 52 (521 etc.) of the partition member 50 (501 etc.) and the edge 19 as shown in FIG. 1.

Figure 4:
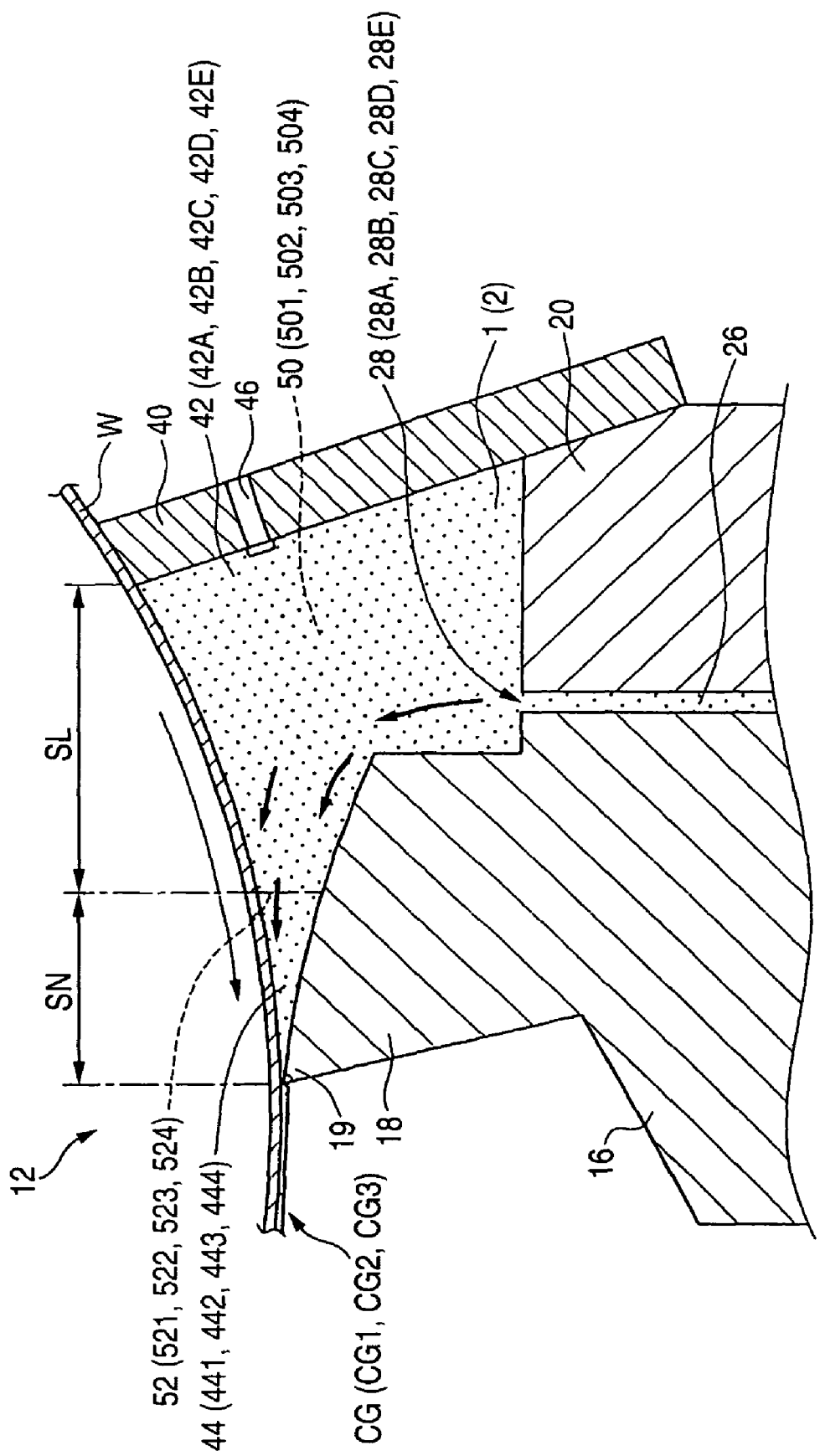
FIG. 4 is an explanatory view showing the behavior of a slurry when the slurry is supplied to the sheet manufacturing apparatus (lip coater) in FIGS. 1 and 2.

As shown in FIG. 4, the first slurry 1 or the second slurry 2 passing through slurry outlet path 26 and injected into the second reservoir chamber 42 from the slurry outlet 28 moves toward the edge 19 as shown by the arrows in FIG. 4. Here, in a separation section SL on the upstream side (right side in FIG. 4) of the front end surface 52 of the partition member 50 shown by the broken line in FIG. 4, the slurry injected into the second reservoir chamber 42 is not mixed with the slurry injected into any adjacent second reservoir chamber, but separated therefrom.

However, in a mixing section SN on the downstream side (left side in FIG. 4) of the front end surface 52, there is no partition member 50. Accordingly, each slurry makes progress not only to the left side but also to the mixing space 44 on the deeper side perpendicular to the paper of FIG. 4 or on the closer side. Thus, the slurries injected into adjacent ones of the second reservoir chambers are mixed with each other. Further, the slurries are applied as a composite ceramic green sheet CG onto the web W while being limited in their application thicknesses by the edge 19. After that, the slurries are dried in a known manner. Thus, the composite ceramic green sheet CG is completed.

The composite ceramic green sheet CG (CG1) formed thus is a striped composite ceramic green sheet CG in which alumina sheet portions R1 (R11, R12 and R13) made of an alumina ceramic material and zirconia sheet portions R2 (R21 and R22) made of a zirconia solid-electrolyte ceramic material are arranged alternately in the spread direction perpendicular to the thickness direction as shown in FIG. 5. In addition, a mixed portion RM (RM1, RM2, RM3, RM4) in which a first sheet material 3 forming the alumina sheet portions R1 and a second sheet material 4 forming the zirconia sheet portions R2 are mixed is provided like a belt between each alumina sheet portion R1 and each zirconia sheet portion R2.

Each first or second sheet material 3 or 4 is a material in which an amount of its solvent removed by drying at the time of film formation has been eliminated from the first or second slurry 1 or 2. Specifically, the material is a component in which water has been eliminated from the first or second slurry 1 or 2, which component chiefly contains a ceramic material, a binder and a colorant and further contains a slight amount of water.

Figure 6:
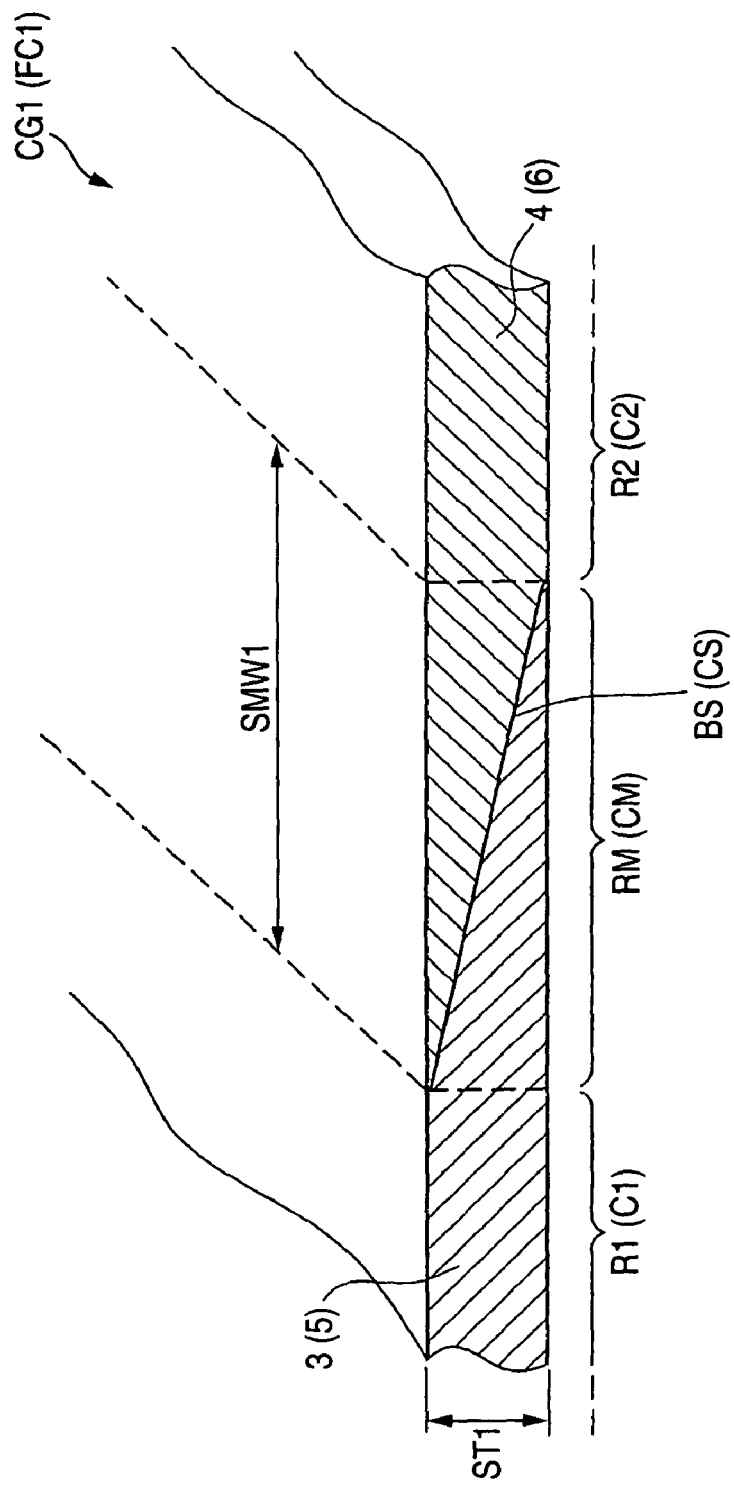
FIG. 6 is an explanatory view showing a sectional structure of a composite ceramic green sheet according to Embodiment 1.

The mixed portion RM has, for example, a form shown in FIG. 6. That is, in the mixed portion RM between the alumina sheet portion R1 and the zirconia sheet portion R2, an interface BS between the first sheet material 3 and the second sheet material 4 tilts obliquely with respect to the thickness direction (up/down direction in FIG. 6). Accordingly, in the direction from the side (left side in FIG. 6) close to the alumina sheet portion R1 toward the side (right side in FIG. 6) close to the zirconia sheet portion R2, the thickness of the portion made of the first sheet material 3 decreases while the thickness of the portion made of the second sheet material 4 increases. In addition, in the composite ceramic green sheet CG1, the mixed width SMW1 of the mixed portion RM is made preferably two or more times, more preferably three or more times, and still more preferably five or more times (for example, 1.0 mm or more) as large as the thickness ST1 (for example, 0.20 mm) of the sheet CG1.

The first and second slurries 1 and 2 are high-viscosity slurries. Therefore, it cannot be considered that the first and second slurries 1 and 2 applied onto the web W beyond the edge 19 are mixed with each other in the mixed portion RM on an extremely large scale while they are dried. Accordingly, it can be considered that when the first and second slurries 1 and 2 have been mixed in the mixed space 44 and applied onto the web W beyond the edge 19, the first and second slurries 1 and 2 are mixed substantially in the form shown in FIG. 6 except reduction in thickness caused by drying.

In such a manner, the first slurry 1 and the second slurry 2 disposed adjacently have the following advantage when they are arranged as in the composite ceramic green sheet CG1 in Embodiment 1.

That is, the first and second slurries 1 and 2 applied onto the web W are dried into a green sheet. In this event, the solvent (water in Embodiment 1) is evaporated so that the sheet becomes thin (shrinks) in the thickness direction and also shrinks in the planar direction (along the web W). However, between the first slurry 1 and the second slurry 2, there is a difference in ratio of the contained solvent (water) or kinds of the contained ceramic material and so on, and there is also difference in shrinkage rate at the time of drying. That is, behaviors of the first and second slurries 1 and 2 are different from each other when the first and second slurries 1 and 2 are formed into a sheet.

Accordingly, when the first slurry 1 and the second slurry 2 abut against each other simply, that is, when the interface between the first slurry 1 and the second slurry 2 (the interface BS between the first sheet material 3 and the second sheet material 4) is aligned substantially in the thickness direction of the sheet, a crack like a tear (split) is apt to appear along the interface due to the difference in behavior at the time of drying shrinkage.

On the other hand, in the aforementioned composite ceramic green sheet CG1, the first sheet material 3 and the second sheet material 4 are mixed over the mixed width SMW1 two or more times as large as the thickness ST1 in the mixed portions RM (RM1 and so on). Accordingly, even if there is a difference in behavior in sheet formation between the first slurry 1 and the second slurry 2, the difference in behavior can be relaxed. Thus, it is possible to obtain a reliable composite ceramic green sheet CG1 in which the mixed portions RM suppress occurrence of cracks.

Further, by firing the composite ceramic green sheet CG1, a composite ceramic layer FC1 is formed. In this event, the first sheet material 3 is formed into an alumina ceramic material 5, the second sheet material 4 is formed into a zirconia solid-electrolyte ceramic material 6, the alumina sheet portions R1 are formed into alumina regions C1, the zirconia sheet portions R2 are formed into zirconia regions C2, and the mixed portions RM are formed into mixed regions CM. Also in this sintering, there is an advantage as follows when the mixed width SMW1 of each mixed portion RM is made two or more times as large as the thickness ST1 in the composite ceramic green sheet CG1.

That is, firing shrinkage occurs in the first sheet material 3 and the second sheet material 4 when the composite ceramic green sheet CG1 is fired. Thus, each sheet material 3, 4 becomes thin (shrinks) in the thickness direction and also shrinks in the planar direction. However, there is a difference between the first sheet material 3 and the second sheet material 4 as to the chemical compositions (alumina ceramic material and zirconia solid-electrolyte ceramic material) of contained ceramic materials, the quantities of contained binders etc., the sintering start temperatures, the shrinkage rates at the time of sintering, the thermal shrinkages caused by the coefficients of thermal expansion after sintering, and so on. That is, the first and second sheet materials 3 and 4 are different from each other as to their firing behaviors when they are sintered.

Accordingly, when the first sheet material 3 and the second sheet material 4 abut against each other simply, that is, when the interface between the first sheet material 3 and the second sheet material 4 is aligned substantially in the thickness direction of the sheet, there occurs a problem as follows. That is, at the time of firing, a crack may appear over or along an interface CS between the alumina ceramic material 5 and the zirconia solid-electrolyte ceramic material 6 in the sintered composite ceramic layer due to the difference in firing behavior when the composite ceramic green sheet is sintered. In addition even if there is no crack immediately after firing, a crack may appear easily over or along the interface CS due to slight stress. It is considered that this is caused by residual stress occurring between the alumina ceramic material and the zirconia solid-electrolyte ceramic material at the time of firing.

On the other hand, in the aforementioned composite ceramic green sheet CG1, the first sheet material 3 and the second sheet material 4 are mixed over the mixed width SMW1 two or more times as large as the thickness ST1 in the mixed portions RM. Accordingly, even if there is a difference in firing behavior between the first sheet material 3 and the second sheet material 4, it is possible to surely form a crack-free composite ceramic layer FC1. This is because the difference in firing behavior can be relaxed due to the existence of the mixed portions RM (mixed regions CM). In addition, due to the existence of the mixed regions CM, it is possible to obtain a reliable composite ceramic layer FC1 in which cracks hardly occur in spite of stress. The mixed width SMW1 may be made larger, three or more times, particularly five or more times as large as the thickness ST1. In this case, the difference in firing behavior is more relaxed so that it is possible to obtain a more reliable composite ceramic layer FC1 in which cracks hardly occur.

Embodiment 1 may be also described as follows. Alumina and zirconia have different characteristics from each other as to sintering temperatures, coefficients of thermal expansion, etc., alumina and zirconia ceramic components are different in firing behavior at the time of firing. However, in the composite ceramic green sheet CG1, as to alumina which is a chief component of the ceramic components (alumina and zirconia. See the first slurry field in Table 1) of the first sheet material 3, the ratio of the alumina to the ceramic components in the mixed portion RM is lower than the ratio (97 wt %) of the alumina to the ceramic components in the first sheet portion 3. On the other hand, as to zirconia which is a chief component of the ceramic components (zirconia and alumina. See the second slurry field in Table 1) of the second sheet material 4, the ratio of the zirconia to the ceramic components in the mixed portion RM is made lower than the ratio (80 wt %) of the zirconia to the ceramic components in the second sheet portion 4.

Accordingly, when the composite ceramic green sheet CG1 is fired, as to firing behavior, the mixed portion RM shows middle firing behavior between that of the first sheet portion 3 and that of the second sheet portion 4 from the point of the ceramic components. Thus, the mixed portion RM relaxes the occurrence of stress caused by the difference in firing behavior between the first sheet portion 3 and the second sheet portion 4 so that it is possible to obtain a composite ceramic layer FC1 in which cracks etc. hardly occur.

Figure 9:
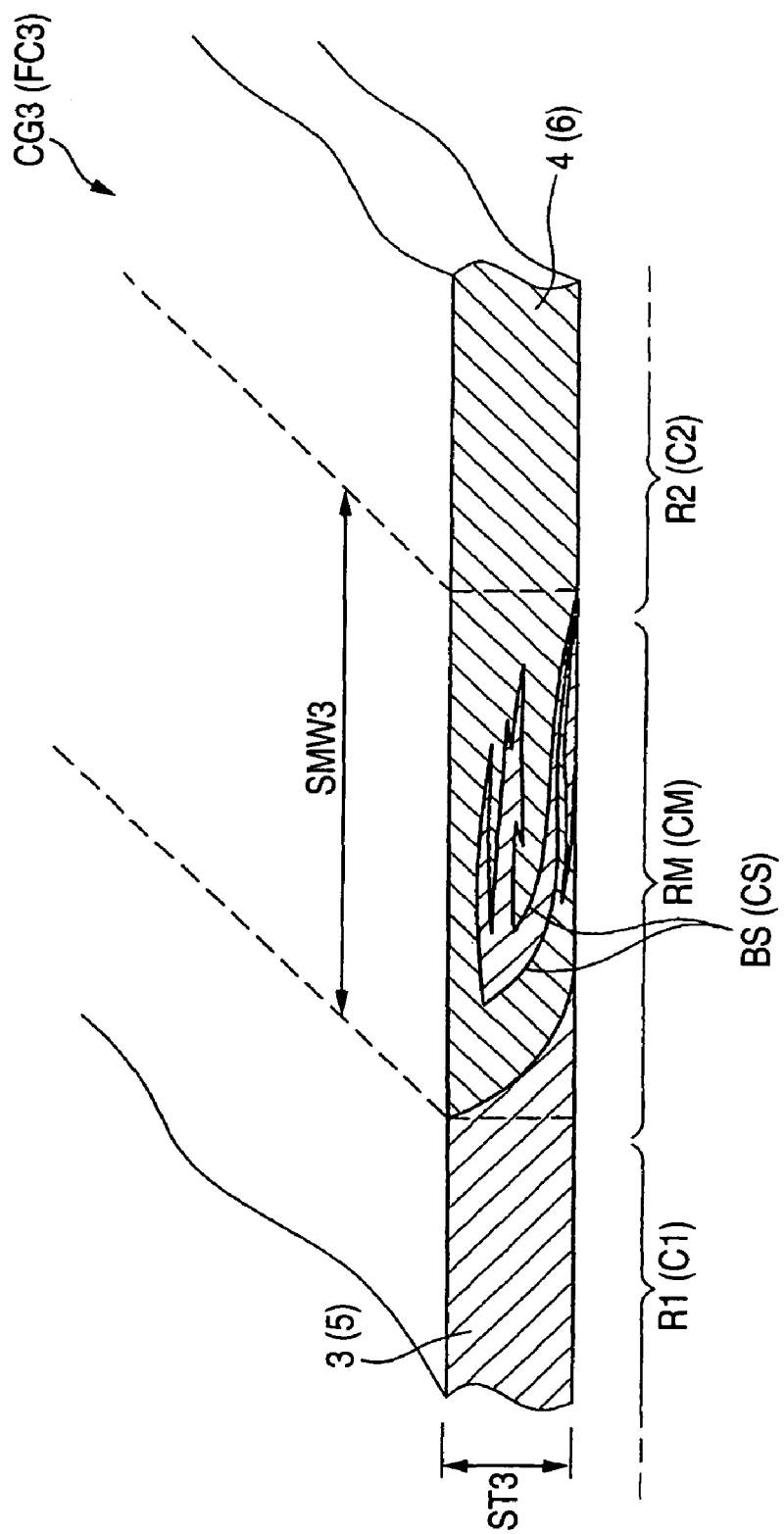
FIG. 9 is an explanatory view showing a sectional structure of a composite ceramic green sheet according to Modification 2.

Further in Embodiment 1, as described previously, the first slurry 1 colored in pink is used. Accordingly, not only is it possible to distinguish the first slurry 1 from the white second slurry 2 by its color tone, but it is also possible to distinguish the pink first sheet material 3 from the white second sheet material easily by its color tone in the composite ceramic green sheet CG1 according to Embodiment 1. Thus, between the alumina sheet portion R1 and the zirconia sheet portion R2, the sheet portions and their border (mixed portion RM) can be distinguished easily so that the composite ceramic green sheet CG1 can be handled easily. In addition, there is another advantage that the condition (see FIGS. 6, 7 and 9) of mixture of the first slurry 1 (first sheet material 3) and the second slurry 2 (second sheet material 4) in the mixed portion RM can be known easily.

(Modification 1)

Figure 7:
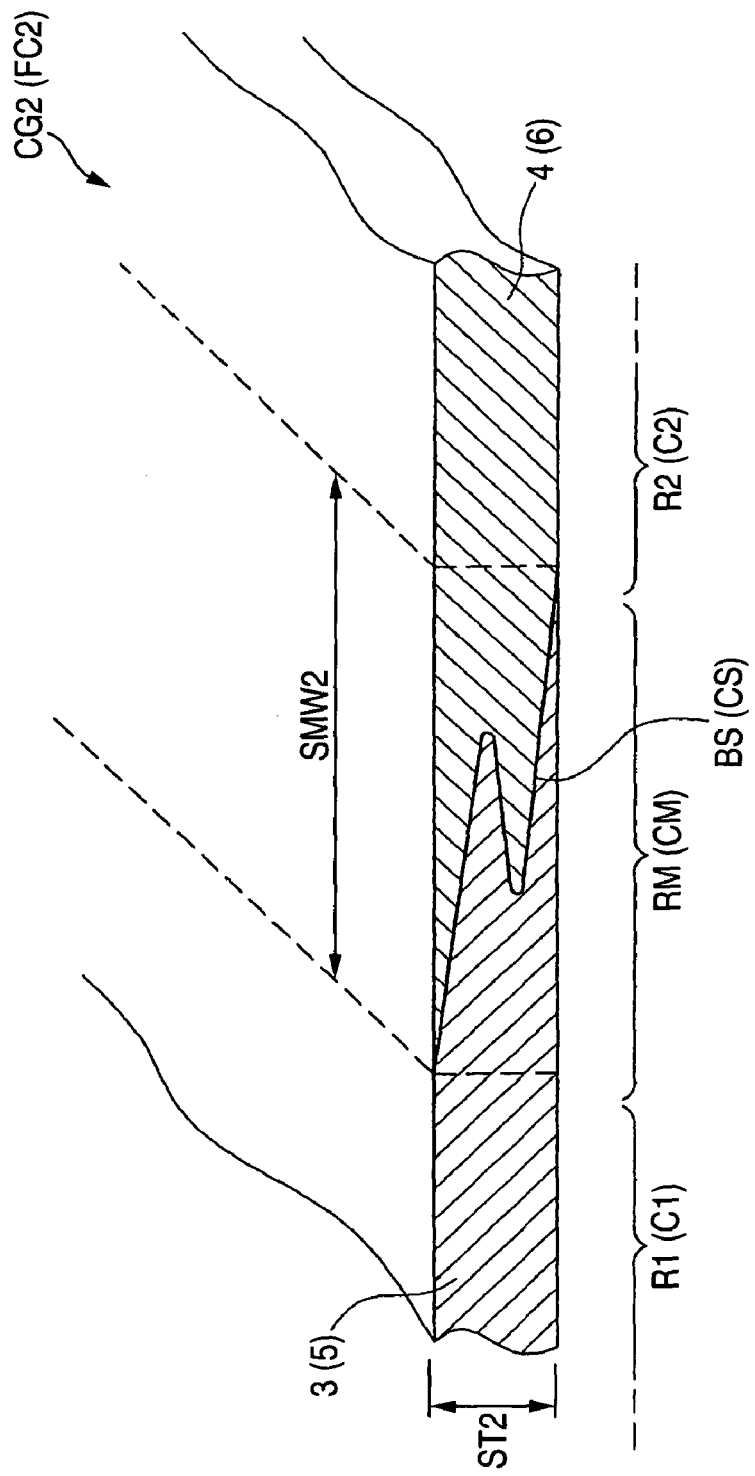
FIG. 7 is an explanatory view showing a sectional structure of a composite ceramic green sheet according to Modification 1.

Further, according to another mixture form of the first sheet material 3 and the second sheet material 4 in the mixed portion RM (or another mixture form of the alumina ceramic material 5 and the zirconia solid-electrolyte ceramic material 6 in the mixed region CM), the interface BS (CS) may be formed into a zigzag shape such as an S-shape in section as shown in FIG. 7. Also in this case, in a composite ceramic green sheet CG2, the mixed width SMW2 of the mixed portion RM is made two or more times as large as the thickness ST2 of the sheet CG2.

In such a manner, in the mixed portion RM, cracks can be prevented from occurring in the composite ceramic green sheet CG2. It is considered that this is because the interface BS between the first sheet material 3 and the second sheet material 4 can be secured so large that the difference in sheet forming behavior between the both can be relaxed due to the large interface BS.

In addition, in the mixed region CM, it can be considered that cracks can be prevented from occurring in a composite ceramic layer FC2 obtained by firing the composite ceramic green sheet CG2. It is considered that this is because the interface CS between the alumina ceramic material 5 and the zirconia solid-electrolyte ceramic material 6 can be secured so large that the difference in firing behavior between the both can be relaxed due to the large interface CS.

In order to form the mixed portion RM in the composite ceramic green sheet CG2 as shown in FIG. 7, the viscosities of the first and second slurries 1 and 2 and the magnitudes of pressures with which the first and second slurries 1 and 2 are pressure-pumped from tubes respectively are set suitably when the sheet manufacturing apparatus 10 shown in Embodiment 1 is used to apply the first and second slurries 1 and 2 to the web W. That is, in the sheet manufacturing apparatus 10, either the form of the composite ceramic green sheet CG1 shown in FIG. 6 or the form of the composite ceramic green sheet CG2 shown in FIG. 7 can be selected by adjusting the viscosities of the first and second slurries 1 and 2, the magnitudes of pressures with which the first and second slurries 1 and 2 are pressure-pumped and so on.

(Modification 2)

Figure 8:
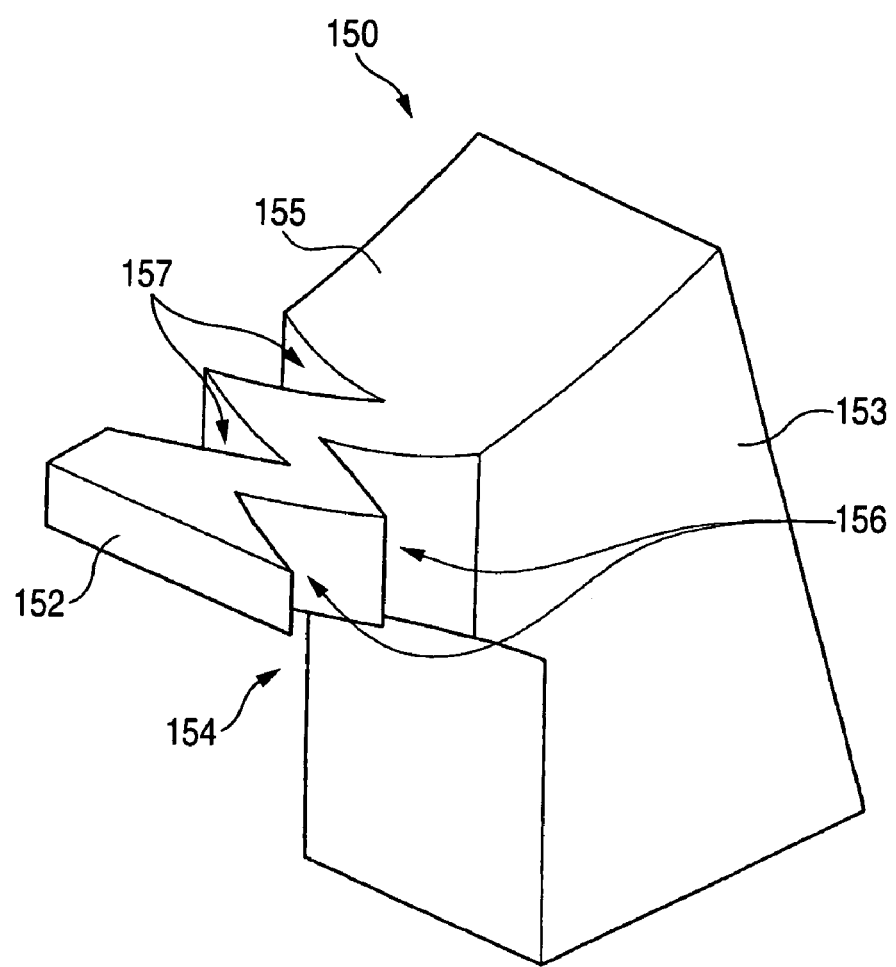
FIG. 8 is an explanatory view showing another shape of a partition member according to Modification 2 for use in the sheet manufacturing apparatus (lip coater) in FIG. 1.

Further, a partition member 150 shown in FIG. 8 may be used in place of each partition member 50 in the aforementioned sheet manufacturing apparatus 10. When the viscosities of the first and second slurries 1 and 2 or the pressures with which the first and second slurries 1 and 2 are pressure-pumped are adjusted by use of the partition members 150, it is possible to manufacture a composite ceramic green sheet CG3 shown in FIG. 9. This reason is considered as follows. That is, due to V-shaped notches 156 and 157 formed in a first side surface 153 and a second side surface 154 of each partition member 150, there occurs a turbulence or a vortex in the flow of the first and second slurries 1 and 2 flowing along the first and second side surfaces 153 and 154. Accordingly, the first and second slurries 1 and 2 are mixed irregularly in the mixing space 44 so that the interface BS between the both is disturbed.

In the green sheet CG3, in each mixed portion RM, the first sheet material 3 and the second sheet material 4 are jigsawed. More specifically, the first sheet material 3 and the second sheet material 4 are jigsawed with each other so as to form a marbling pattern in section. Also in this case, the mixed width SMW3 of the mixed portion RM is made two or more times as large as the thickness ST3 of the composite ceramic green sheet CG3.

In such a manner, in the mixed portion RM, cracks can be prevented from occurring in the composite ceramic green sheet CG3. It is considered that this is because the complicatedly jigsawed interface BS between the first sheet material 3 and the second sheet material 4 can secure its area so large that the difference in sheet forming behavior between the both can be relaxed due to the large interface BS.

In addition, in the mixed region CM, it can be considered that cracks can be prevented from occurring in a composite ceramic layer FC3 obtained by firing the green sheet CG3. It is considered that this is because the complicatedly jigsawed interface CS between the alumina ceramic material 5 and the zirconia solid-electrolyte ceramic material 6 can secure its area so particularly large that the difference in firing behavior between the both can be relaxed due to the large interface CS.

Next, a gas sensor device (ceramic sintered body) 100 (see FIG. 11) is manufactured using the composite ceramic green sheet CG1 according to Embodiment 1 (or Modification 1 or 2) described above.

BACKGROUND-ART EXAMPLE

Prior to the description of the gas sensor device 100, the structure of a background-art gas sensor device GS will be described with reference to FIG. 10. This gas sensor device GS is a gas sensor device fundamentally comprised of first and second zirconia solid-electrolyte layers Z1 and Z2 made of a zirconia solid-electrolyte ceramic material. Of them, the first zirconia solid-electrolyte layer Z1 (hereinafter referred to as "layer Z1" simply) has a function as a solid electrolyte for detecting gas. On the other hand, the second zirconia solid-electrolyte layer Z2 is used for reinforcement of the layer Z1.

A through hole ZTH1 is made in the first zirconia solid-electrolyte layer Z1. A first alumina insulation coat layer AL1 is disposed on a surface (upper surface in FIG. 10) Z1b of the layer Z1. The first alumina insulation coat layer AL1 is formed by co-firing alumina paste applied onto the surface Z1b. In the first alumina insulation coat layer AL1, a through hole ATH1 is formed in a position corresponding to the through hole ZTH1, and a rectangular electrode window AH1 is formed on the front end side (right in FIG. 10).

In the same manner, also on a back surface (lower surface in FIG. 10) Z1c of the first zirconia solid-electrolyte layer Z1, a second alumina insulation coat layer AL2 is disposed. The second alumina insulation coat layer AL2 is formed by co-firing alumina paste applied onto the surface Z1c. Also in the second alumina insulation coat layer AL2, a through hole ATH2 is formed in a position corresponding to the through hole ZTH1, and a rectangular electrode window AH2 is formed on the front end side (right in FIG. 10).

Further, first and second electrode layers EL1 and EL2 made of platinum are formed on the first alumina insulation coat layer AL1 by co-sintering platinum paste applied thereto. A fourth electrode EL4 made of platinum is formed under the second alumina insulation coat layer AL2 likewise.

Of them, the first electrode layer EL1 has a wide rectangular electrode portion EL1A in its front end portion. The electrode portion EL1A is in direct contact with the surface Z1b of the first zirconia solid-electrolyte layer Z1 through the electrode window AH1 of the first alumina insulation coat layer AL1. On the other hand, of the first electrode layer EL1, the portion where the first alumina insulation coat layer AL1 is provided between the first electrode layer EL1 and the first zirconia solid-electrolyte layer Z1 is insulated from the first zirconia solid-electrolyte layer Z1. In addition, a pad portion EL1B made slightly wide serves as an electrode pad portion for transmitting the output of the gas sensor device GS to the outside. The electrode portion EL1A and the pad portion EL1B are connected through a slightly narrow wiring portion EL1C.

In the same manner, the fourth electrode layer EL4 has a wide rectangular electrode portion EL4A in its front end portion. The electrode portion EL4A is in direct contact with the back surface Z1c of the first zirconia solid-electrolyte layer Z1 through the electrode window AH2 of the second alumina insulation coat layer AL2. The electrode portion EL4A of the fourth electrode layer EL4 is opposite to the electrode portion EL1A of the first electrode layer EL1. On the other hand, of the fourth electrode layer EL4, the portion where the second alumina insulation coat layer AL2 is provided between the fourth electrode layer EL4 and the first zirconia solid-electrolyte layer Z1 is insulated from the first zirconia solid-electrolyte layer Z1. In addition, a pad portion EL4B made slightly wide also serves as an electrode pad portion. The electrode portion EL4A and the pad portion EL4B are connected through a slightly narrow wiring portion EL4C.

Further, the second electrode layer EL2 has almost the same shape as the pad portion EL1B of the first electrode layer EL1. The second electrode layer EL2 is electrically connected to the pad portion EL4B of the fourth electrode layer EL4 through a cylindrical through hole electrode layer EL3 in the through hole ZTH1 of the first zirconia solid-electrolyte layer Z1. The through hole electrode layer EL3 is formed concurrently with the second electrode layer EL2.

The first zirconia solid-electrolyte layer Z1 is a solid electrolyte having ion conductivity. Therefore, in order to insulate the through hole electrode layer EL3 from the first zirconia solid-electrolyte layer Z1, an alumina insulation through hole layer AL4 is formed by firing alumina paste applied to the inner wall surface of the through hole ZTH1. The through hole electrode layer EL3 is formed on the inner side of the alumina insulation through hole layer AL4.

Further, the reinforcing second zirconia solid-electrolyte layer Z2 is provided under the fourth electrode layer EL4.

In such a manner, in the background-art gas sensor device, gas can be detected by use of the ion conductivity of the zirconia solid electrolyte. However, due to use of a ceramic layer (the laser Z1 in this example) made of a single ceramic material (that is, the zirconia solid-electrolyte ceramic material), any other portion than the electrode portions EL1A and EL4A has to be insulated using the first and second alumina insulation coat layers AL1 and AL2 in order to lead the first and fourth electrode layers EL1 and EL4. Thus, both the structure and the manufacturing process must be complicated.

In addition, also in the through hole ZTH1 of the layer Z1, the through hole electrode layer EL3 is formed inside the alumina insulation through hole layer AL4 formed for insulation. Accordingly, also from this point, both the structure and the manufacturing process must be complicated.

Further, in order to ensure insulation between the through hole electrode layer EL3 and the layer Z1, the alumina insulation through hole layer AL4 has to be formed surely, and the through hole electrode layer EL3 has to be allowed to be formed inside the alumina insulation through hole layer AL4. To this end, it is inevitable to increase the diameter of the through hole ZTH1. This is an obstacle to miniaturization of the gas sensor device.

Embodiment 2

Figure 11:
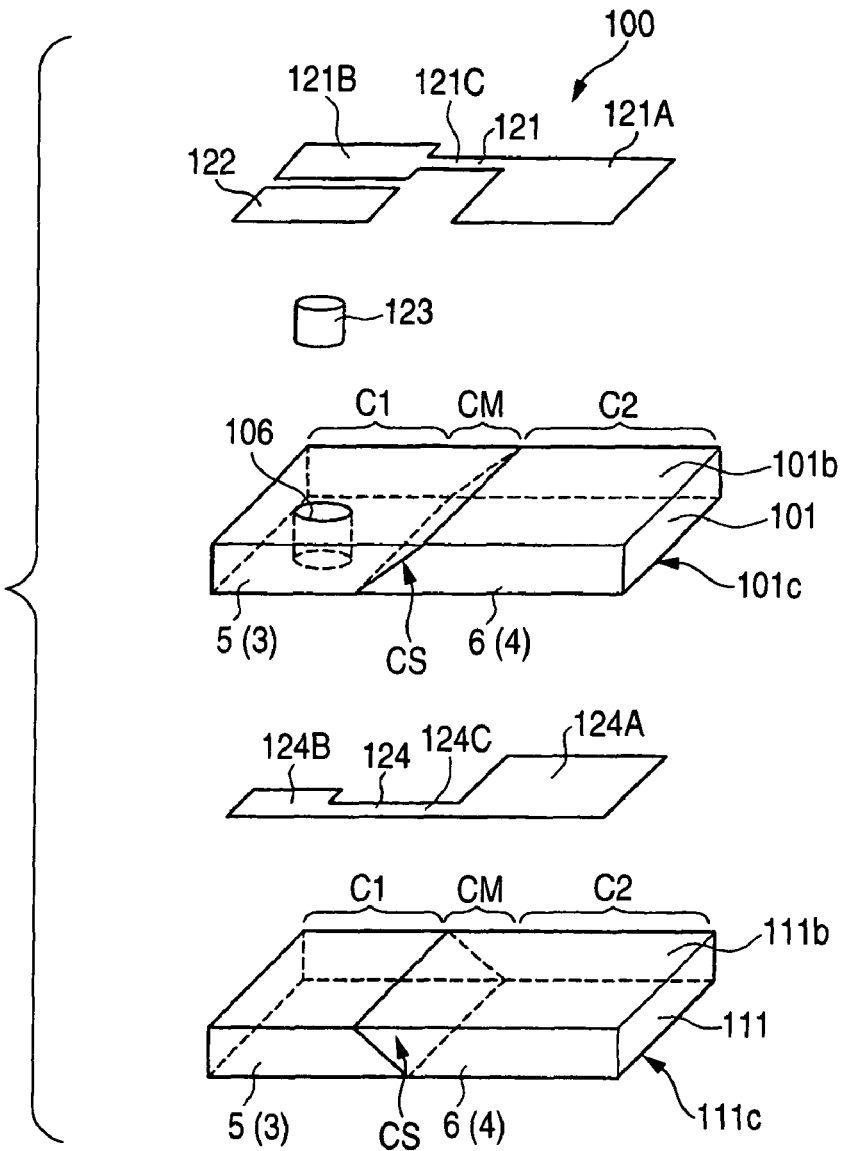
FIG. 11 is an explanatory view showing a structure of a gas sensor device according to Embodiment 2 using the aforementioned composite ceramic green sheet according to Embodiment 1.

In contrast, a gas sensor device 100 shown in FIG. 11 is miniaturized with a simple structure which can be understood easily. Description will be made about the gas sensor device 100.

This gas sensor device 100 is a gas sensor device fundamentally comprised of composite ceramic layers 101 and 111 each made of a composite of an alumina ceramic material 5 and a zirconia solid-electrolyte ceramic material 6. Of them, the zirconia solid-electrolyte ceramic material 6 (zirconia region C2) of the first composite ceramic layer 101 has a function as a solid electrolyte for detecting gas. On the other hand, the second composite ceramic layer 111 is used for reinforcement of the composite ceramic layer 101.

The first composite ceramic layer 101 is formed out of the aforementioned composite ceramic green sheet CG1 according to Embodiment 1. The first composite ceramic layer 101 is divided into an alumina region C1 made of the alumina ceramic material 5, the zirconia region C2 made of the zirconia solid-electrolyte ceramic material 6, and a mixed region CM provided between the alumina region C1 and the zirconia region C2. In the mixed region CM, the alumina ceramic material 5 and the zirconia solid-electrolyte ceramic material 6 are mixed. Of these regions, the alumina region C1 has a through hole 106. Inside the through hole 106, a via conductor 123 made of platinum is formed by firing platinum paste charged into the through hole 106. Further, differently from the background-art example described previously, first, second and fourth electrode layers 121, 122 and 124 made of platinum are formed in the surface and back surface 101b and 101c of the first composite ceramic layer 101 without formation of any alumina insulation coat layer. The first, second and fourth electrode layers 121, 122 and 124 are formed by co-sintering platinum paste applied to the surface and back surface 101b and 101c.

Of them, the first electrode layer 121 has a wide rectangular electrode portion 121A in its front end portion. The electrode portion 121A is in direct contact with the zirconia region C2 of the first composite ceramic layer 101. On the other hand, of the first electrode layer 121, the portion extracted on the base end side (left side in FIG. 11) of the electrode portion 121A is insulated from the zirconia solid-electrolyte ceramic material 6 at least in the surface position of the alumina region C1, specifically in a pad portion 121B. The pad portion 121B serves as an electrode pad portion for transmitting the output of the gas sensor device 100 to the outside. The electrode portion 121A and the pad portion 121B are connected through a slightly narrow wiring portion 121C.

In the same manner, the fourth electrode layer 124 has a wide rectangular electrode portion 124A in its front end portion. The electrode portion 124A is in direct contact with the back surface of the zirconia region C2 of the first composite ceramic layer 101. On the other hand, of the fourth electrode layer 124, the portion extracted on the base end side (left side in FIG. 11) of the electrode portion 124A is insulated from the zirconia solid-electrolyte ceramic material 6 at least in the back surface position of the alumina region C1, specifically in a pad portion 124B. The pad portion 124B serves as an electrode pad portion for connecting to the second electrode layer 122 through the via conductor 123. The second electrode layer 122 will be described next. The electrode portion 124A and the pad portion 124B are connected through a slightly narrow wiring portion 124C.

Further, the second electrode layer 122 has almost the same shape as the pad portion 121B of the first electrode layer 121. The second electrode layer 122 is in contact with the surface of the alumina region C1 of the first composite ceramic layer 101, and electrically connected to the pad portion 124B of the fourth electrode layer 124 through the via conductor 123.

Differently from the aforementioned background-art example, it is not necessary to form an alumina insulation through hole layer in order to insulate the via conductor 123 from the zirconia solid-electrolyte ceramic material 6. It is because the through hole 106 is formed in the alumina region C1 which is insulating.

Further, the reinforcing second composite ceramic layer 111 is provided under the fourth electrode layer 124.

In such a manner, in the gas sensor device 100 according to Embodiment 2, gas can be detected by use of the ion conductivity of the zirconia solid electrolyte because the composite ceramic layer 101 is used. In addition, it is not necessary to form any alumina insulation coat layer in order to lead the first and fourth electrode layers 121 and 124. Therefore, both the structure and the manufacturing process are simple.

In addition, since it is not necessary to secure insulation between the via conductor 123 and the zirconia solid-electrolyte ceramic material, it is not necessary to form any alumina insulation through hole layer. Therefore, both the structure and the manufacturing process are simple.

Further, since it is not necessary to form any alumina insulation through hole layer, the diameter of the through hole 106 may be made small. Thus, it is advantageous in miniaturization of the gas sensor device.

Figure 10:
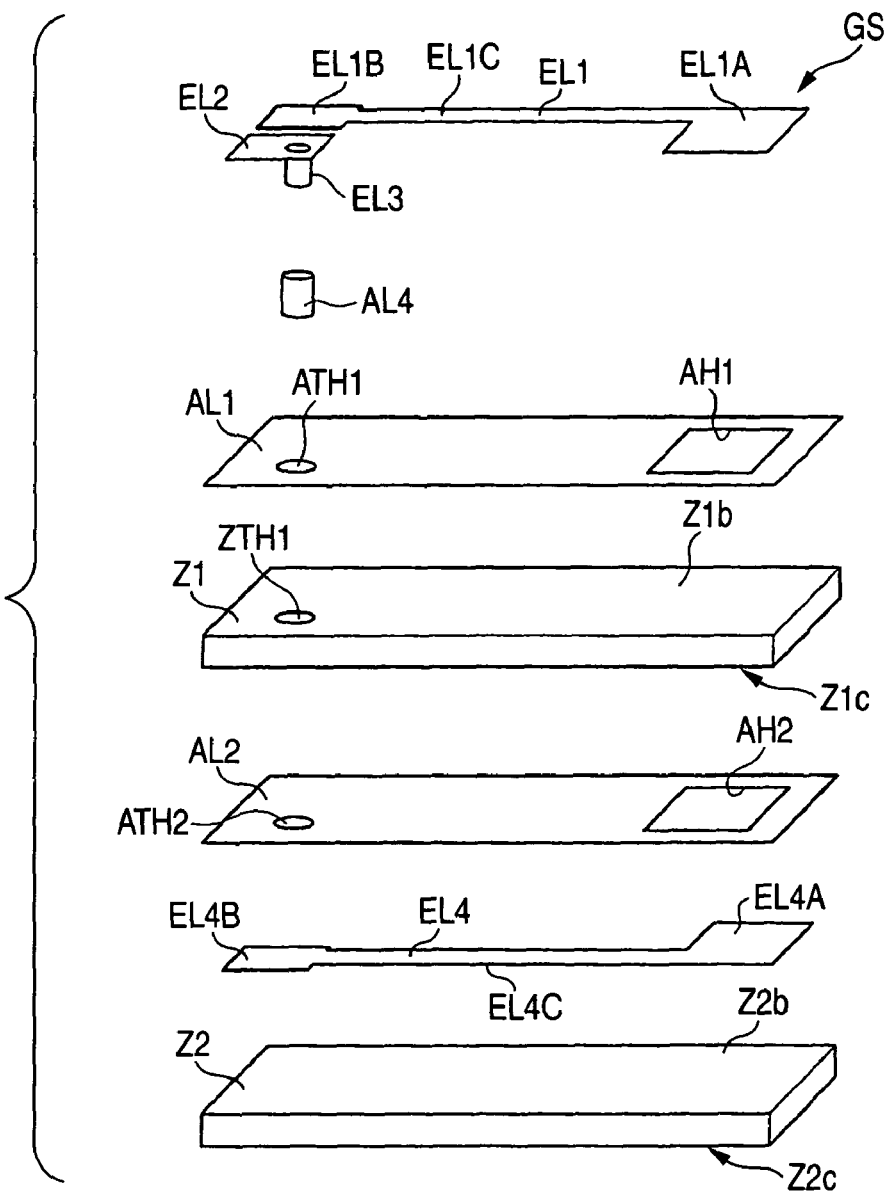
FIG. 10 is an explanatory view showing an example of a structure of a gas sensor using a background-art ceramic green sheet.

In fact, as can be understood easily by comparison between FIG. 10 and FIG. 11, the gas sensor device 100 according to Embodiment 2 can be miniaturized on a large scale.

In addition, in the gas sensor device 100 according to Embodiment 2, each first, second composite ceramic layer 101, 111 has a mixed region CM between the alumina region C1 and the zirconia region C2. The mixed region CM has a width two or more times as large as the thickness of the layer. More specifically, the mixed region CM is provided between the alumina region C1 and the zirconia region C2. The mixed region CM has a width (mixed width) two or more times as large as the thickness of each composite ceramic layer 101, 111 in view of a section parallel to the longitudinal direction of the composite ceramic layer 101, 111 and along the thickness direction. Accordingly, cracks hardly occur in the composite ceramic layer 101, 111 on and after manufacturing the gas sensor device 100 by co-firing. Thus, the gas sensor device 100 becomes reliable.

In Embodiment 2, the two composite ceramic layers 101 and 111 having the mixed regions CM in each of which the interface CS between the two ceramic materials cross each other obliquely with respect to the thickness direction of each layer as shown in Embodiment 1 (see FIG. 6) are used on top of each other. In such a case, the direction of the interface CS may be selected as shown in FIG. 11. That is, when the two composite ceramic layers 101 and 111 are laid on top of each other, the portions made of one and the same ceramic material may be made to abut against each other over a width as long as possible (over an area as wide as possible). Specifically in this embodiment, the form of a mixed region CM in which the interface CS moves upward as goes from left to right in FIG. 11 is selected for the first composite ceramic layer 101. On the other hand, the form of a mixed region CM in which the interface CS moves downward as goes from left to right in FIG. 11 is selected for the second composite ceramic layer 111.

The gas sensor device 100 according to Embodiment 2 may be manufactured as follows. That is, two composite ceramic green sheets are prepared, and the through hole 106 is made in one of the green sheets. Further the through hole 106 is filled with platinum paste, and further the first, second and fourth electrodes are printed on the surface and back surface of the green sheet using platinum paste. Further, the other composite ceramic green sheet is laminated and co-fired. Thus, the gas sensor device 100 can be obtained.

Embodiment 3

Alternatively, the following gas sensor device (ceramic sintered body) 200 (see FIG. 12) can be manufactured using a composite ceramic green sheet CG1 or the like according to Embodiment 1 or Modification 1 or 2 described previously.

The gas sensor device 200 according to Embodiment 3 has first and second composite ceramic layers 201 and 211. Of them, the first composite ceramic layer 201 is comprised of an alumina region C1, a zirconia region C2 and a mixed region CM in which an alumina ceramic material 5 and a zirconia solid-electrolyte ceramic material 6 are mixed. That is, a composite ceramic green sheet according to Embodiment 1 or Modification 1 or 2 is used and sintered.

On the other hand, the second composite ceramic layer 211 is comprised of a dense alumina region CA1, a porous alumina region CA2 and a mixed region CAM in which a dense alumina ceramic material 7 and a porous alumina ceramic material 8 are mixed. That is, a composite ceramic green sheet is manufactured out of two kinds of slurries shown in Table 2, in the same manner as in Embodiment 1 or Embodiment 2. The composite ceramic green sheet is sintered. As is understood easily with reference to Table 2, carbon powder as porosifier is mixed into a second slurry to be formed into the porous alumina region CA2. The carbon powder is burnt and gasified at the time of firing, so as to form the porous alumina region CA2 having an alumina skeleton.

TABLE 2

| prepared raw materials | first slurry | second slurry |
|---|---|---|
| alumina powder | 97.0 | 97.0 |
| zirconia (containing $Y_2O_3$) powder | 3.0 | 3.0 |
| urethane resin water-based emulsion | 20.0 | 25.0 |
| Plasticizer | 2.0 | 2.5 |
| porosifier (carbon powder) | — | 35.0 |
| Dispersant | 0.2 | 0.2 |
| colorant (rhodamine) | $10^{-4}$ | — |
| Antifoamer | 0.2 | 0.2 |
| Water | 56.0 | 92.0 | per 100 parts by weight of ceramic component

Figure 12:
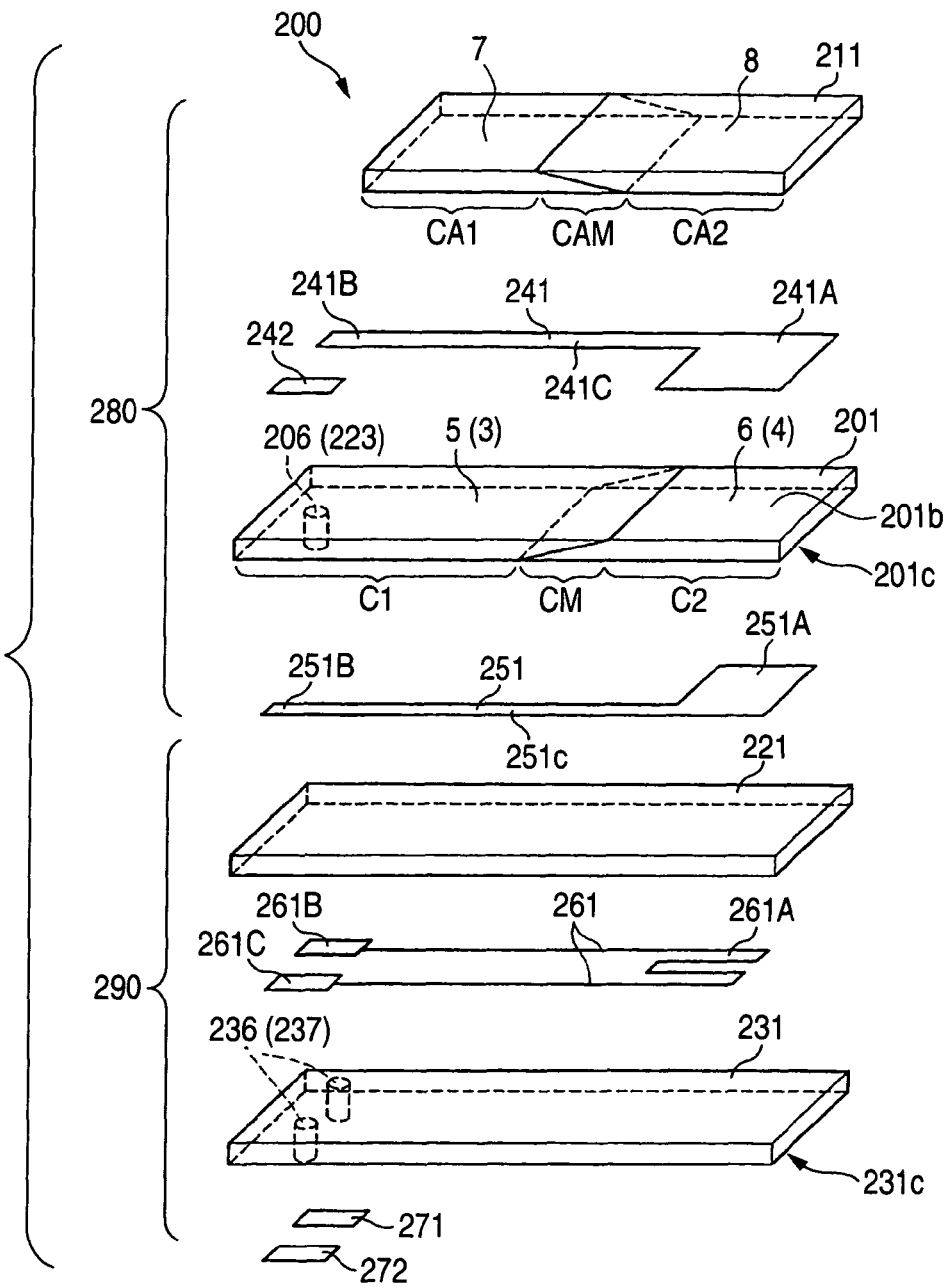
FIG. 12 is an explanatory view showing another structure of a gas sensor device according to Embodiment 3 using the aforementioned composite ceramic green sheet according to Embodiment 1.

The gas sensor device 200 shown in FIG. 12 is a gas sensor device with a heater. As is understood easily in comparison with the background-art example (see FIG. 10), each part of the gas sensor device has a simpler structure than in the background art. Description will be made about the gas sensor device 200.

As described above, the gas sensor device 200 is roughly constituted by a gas sensor device portion 280 serving as a gas sensor, and a heater portion 290 for heating a zirconia solid-electrolyte ceramic material of the gas sensor device portion 280.

Of them, the gas sensor device portion 280 is fundamentally comprised of a first composite ceramic layer 201 made of a composite of an alumina ceramic material 5 and a zirconia solid-electrolyte ceramic material 6. The first composite ceramic layer 201 is comprised of an alumina region C1 made of the alumina ceramic material 5, a zirconia region C2 made of the zirconia solid-electrolyte ceramic material 6, and a mixed region CM which is provided between the alumina region C1 and the zirconia region C2 and in which the alumina ceramic material 5 and the zirconia solid-electrolyte ceramic material 6 are mixed. Of them, the zirconia region C2 (zirconia solid-electrolyte ceramic material 6) has a function as a solid electrolyte for detecting gas.

In addition, the gas sensor device portion 280 includes a second composite ceramic layer 211. The second composite ceramic layer 211 is comprised of a dense alumina region CA1 made of a dense alumina ceramic material 7 the same as the alumina ceramic material 5, a porous alumina region CA2 made of a porous alumina ceramic material 8, and a mixed region CAM which is provided between the dense alumina region CA1 and the porous alumina region CA2 and in which the dense alumina ceramic material 7 and the porous alumina ceramic material 8 are mixed.

In the second composite ceramic layer 211, the dense alumina region CA1 chiefly serves to reinforce the composite ceramic layer 201, while the porous alumina region CA2 is used for securing of gas circulation to the zirconia region C2 surface and an electrode portion 241A which will be described next, while used for chemical protection of these regions from poisoning substances such as phosphor, silicon, etc.

The first composite ceramic layer 201 is formed out of the aforementioned composite ceramic green sheet CG1 according to Embodiment 1. A through hole 206 is made in the alumina region C1. Inside the through hole 206, a via conductor 223 made of platinum is formed by firing platinum paste charged into the through hole 206. Further, in the same manner as Embodiment 2 (see FIG. 11) and differently from the background-art example described previously (see FIG. 10), first, second and fourth electrode layers 241, 242 and 251 made of platinum are formed in the surface and back surface 201b and 201c of the first composite ceramic layer 201 without forming any alumina insulation coat layer. The first, second and fourth electrode layers 241, 242 and 251 are formed by co-sintering platinum paste applied to the surface and back surface 201b and 201c.

Of them, the first electrode layer 241 has a wide rectangular electrode portion 241A in its front end portion. The electrode portion 241A is in direct contact with the surface of the zirconia region C2 of the first composite ceramic layer 201. On the other hand, of the first electrode layer 241, the portion extracted on the base end side (left side in FIG. 12) of the electrode portion 121A is insulated from the zirconia solid-electrolyte ceramic material 6 at least in the surface position of the alumina region C1, specifically in a pad portion 241B. The pad portion 241B serves as an electrode pad portion for transmitting the output of the gas sensor device 200 to the outside. The electrode portion 241A and the pad portion 241B are connected through a wiring portion 241.

In the same manner, the fourth electrode layer 251 has a wide rectangular electrode portion 251A in its front end portion. The fourth electrode portion 251A is in direct contact with the back surface of the zirconia region C2 of the first composite ceramic layer 201. On the other hand, of the fourth electrode layer 251, the portion extracted on the base end side (left side in FIG. 12) of the electrode portion 251A is insulated from the zirconia solid-electrolyte ceramic material 6 at least in the back surface position of the alumina region C1, specifically in a pad portion 251B. The pad portion 251B serves as an electrode pad portion for connecting to the second electrode layer 242 through the via conductor 223. The second electrode layer 242 will be described next. The electrode portion 251A and the pad portion 251B are connected through a wiring portion 251C.

Further, the second electrode layer 242 has almost the same shape as the pad portion 241B of the first electrode layer 241. The second electrode layer 242 is in contact with the surface of the alumina region C1 of the first composite ceramic layer 201, and electrically connected to the pad portion 251B of the fourth electrode layer 251 through the via conductor 223.

On the same manner as in Embodiment 2 and differently from the aforementioned background-art example, it is not necessary to form an alumina insulation through hole layer in order to insulate the via conductor 223 from the zirconia solid-electrolyte ceramic material 6. It is because the through hole 206 is formed in the alumina region C1 which is insulating.

Further, the aforementioned reinforcing second composite ceramic layer 211 is provided above the first and second electrode layers 241 and 242.

Next, description will be made about the heater portion 290. The heater portion 290 includes a first alumina layer 221, a second alumina layer 231 and a heater wiring layer 261 provided between the first and second alumina layers 221 and 231. The first and second alumina layers 221 and 231 are chiefly made of an alumina ceramic material, and have almost the same dimensions as the aforementioned first composite ceramic layer 211 in the planar direction. The heater wiring layer 261 includes a heating portion 261A on its front end side (right side in FIG. 12). The heating portion 261A is thinned and folded zigzag under the electrode portions 241A and 251A. Slightly wide pad portions 261B and 261C are formed in the opposite ends on the base end side (left side in FIG. 12). Each pad portion 261B, 261C is connected to a pad layer 271, 272 through a via conductor 237 charged into a through hole 236 formed in the second alumina layer 231. The pad layer 271, 272 is formed in the base end portion of a back surface 231c of the second alumina layer 231.

Accordingly, in the gas sensor device 200 according to Embodiment 3, a voltage is applied between the pads 271 and 272 so as to apply a current therebetween and heat the heating portion 261A of the heater wiring 261. Thus, the zirconia region C2 of the first composite ceramic layer 210 is heated to have oxygen ion conductivity. As a result, gas can be detected in the gas sensor device portion 280. Specifically, the gas sensor device portion 280 serves as an oxygen concentration cell device. Thus, an electromotive force (output) generated in the oxygen concentration cell device can be obtained between the pad portion 241B and the second electrode-layer 242.

The heater portion 290 also serves as a reinforcement of the gas sensor device portion 280.

In such a manner, in the gas sensor device 200 according to Embodiment 3, due to use of the first composite ceramic layer 201, gas can be detected using the ion conductivity of the zirconia solid-electrolyte, while it is not necessary to form any alumina insulation coat layer for leading the first and fourth electrode layers 241 and 251. In addition, since it is not necessary to secure insulation between the via conductor 223 and the zirconia solid-electrolyte ceramic material, it is not necessary to form any alumina insulation through hole layer. Thus, the gas sensor device 200 is simple in both its structure and its manufacturing process.

In addition, also in the gas sensor device 200 according to Embodiment 3, the first composite ceramic layer 201 has a mixed region CM between the alumina region C1 and the zirconia region C2. The mixed region CM has a mixed width two or more times as large as the thickness of the first composite ceramic layer 201. Further, the second composite ceramic layer 211 has a mixed region CAM between the dense alumina region CA1 and the porous alumina region CA2. The mixed region CAM has a mixed width two or more times as large as the thickness of the second composite ceramic layer 211. Accordingly, cracks hardly occur in the composite ceramic layers 201 and 211 on and after manufacturing the gas sensor device 200 by co-firing. Thus, the gas sensor device 200 becomes reliable.

(Modification 3)

Next, description will be made about a modification of the aforementioned gas sensor device according to Embodiment 3. In the aforementioned gas sensor device 200, in addition to the first composite ceramic layer 201, the second composite ceramic layer 211 comprised of the dense alumina region CA1, the porous alumina region CA2 and the mixed region CAM in which the dense alumina ceramic material 7 and the porous alumina ceramic material 8 are mixed is laminated to the first composite ceramic layer 201 (see FIG. 12).

Figure 14:
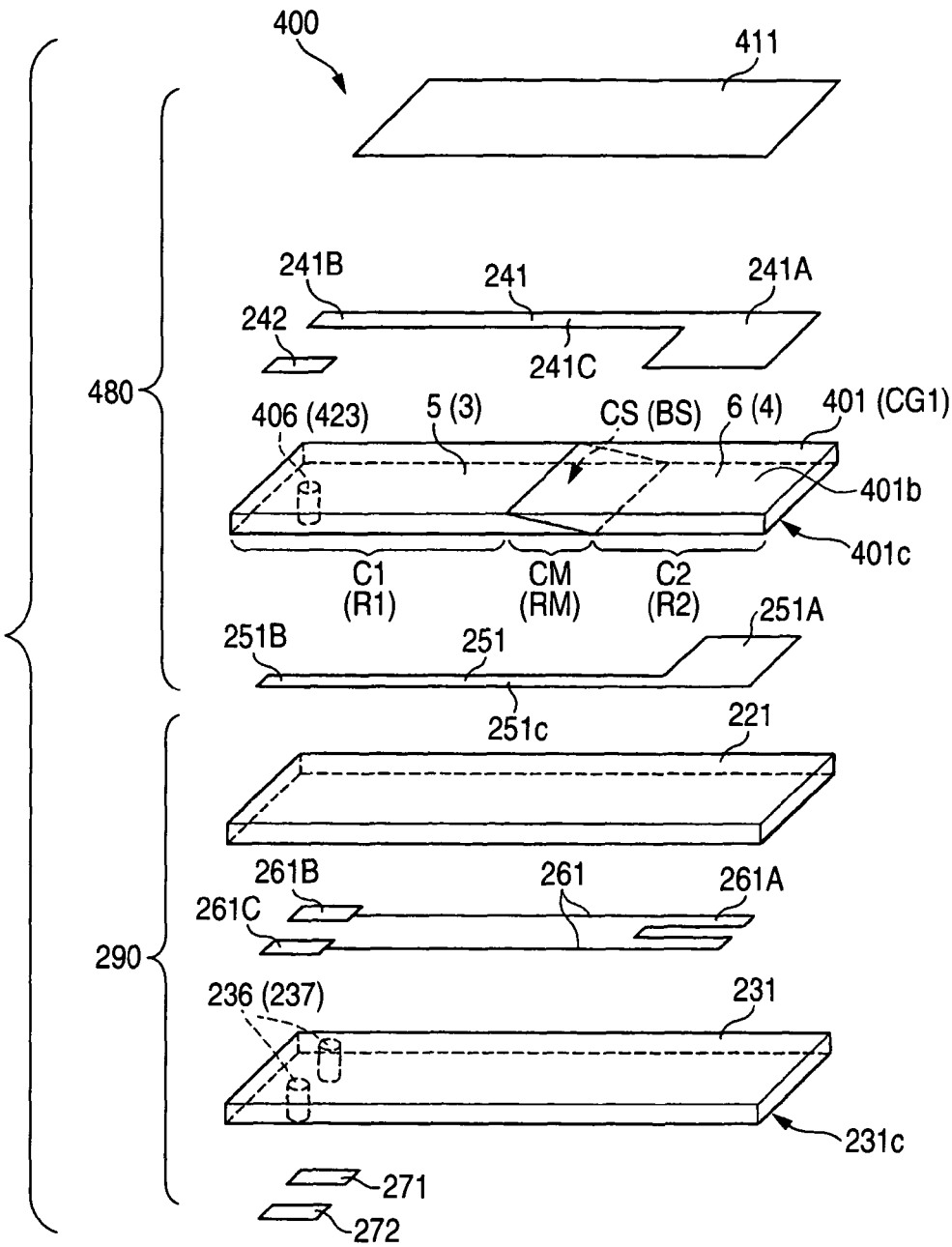
FIG. 14 is an explanatory view showing another structure of a gas sensor device according to Modification 3 using the aforementioned composite ceramic green sheet according to Embodiment 1.

A gas sensor device 400 according to Modification 3 (see FIG. 14) has a difference from the gas sensor device 200 according to Embodiment 3 as follows. That is, in a gas sensor device portion 480, an alumina protective layer 411 is formed by printing or thermal spraying in place of the second composite ceramic layer 211, so as to chemically protect the electrode portion 241A or the wiring portion 241B from poisoning substances such as phosphor, silicon, etc. while securing gas circulation to the electrode portion 241A of the fist electrode layer 241.

Further, in the gas sensor device 400 according to Modification 3, a first composite ceramic layer 401 is formed using the composite ceramic green sheet CG1 according to Embodiment 1 in the same manner as in Embodiment 3. However, as is understood easily with reference to FIGS. 12 and 14 in contrast, the first composite ceramic layer 401 is used in a two-side relationship reverse to the first composite ceramic layer 201 according to Embodiment 3.

That is, the first composite ceramic layer 401 is comprised of an alumina region C1 made of an alumina ceramic material 5, a zirconia region C2 made of a zirconia solid-electrolyte ceramic material 6, and a mixed region CM which is provided between the alumina region C1 and the zirconia region C2 and in which the alumina ceramic material 5 and the zirconia solid-electrolyte ceramic material 6 are mixed. Modification 3 is the same as Embodiment 3 in this point. However, in Modification 3, lamination is performed in consideration of the surface and back surface of the first composite ceramic layer 401, that is, the composite ceramic green sheet CG1, so that the first alumina layer 221 fired concurrently with the first composite ceramic layer 401 abuts against the alumina ceramic material 5 in the mixed region CM.

There is a difference in material, coefficient of thermal expansion, etc. between the alumina forming the first alumina layer 221 and the zirconia solid-electrolyte ceramic material 6 used for the first composite ceramic layer 401. Thus, there is also a difference in firing behavior at the time of co-firing. Accordingly, it is advantageous to reduce the contact area between the first alumina layer 221 and the zirconia solid-electrolyte ceramic material 6 so as to reduce stress caused by the difference in firing behavior. To this end, as in Modification 3, lamination is performed so that the alumina ceramic material 5 of the mixed region CM appears on the back surface 401c side. In such a manner, it is possible to reduce stress caused by the difference in firing behavior between the first alumina layer 221 and the first composite ceramic layer 401, particularly between the first alumina layer 221 and the mixed region CM of the first composite ceramic layer 401. As a result, it is possible to suppress cracks that might occur due to such stress.

Further, in the gas sensor device 400 according to Modification 3, gas detection is performed using a voltage generated between the first electrode layer 241 and the fourth electrode layer 251. Further, the gas sensor device 400 includes a heater wiring layer 261. The insulating first alumina layer 221 is present between the heater wiring layer 261 and the gas sensor device portion 480. However, for example, when there is a difference in potential between the first electrode layer 241 and the heater wiring layer 261, a slight leakage current may flow into the first electrode layer 241 through the first alumina layer 221 and the first composite ceramic layer 401 so as to give influence to the gas sensor output. In the first composite ceramic layer 401, a leakage current is apt to flow particularly via the zirconia solid-electrolyte ceramic material 6 which will have conductivity due to heating.

In contrast, in the gas sensor device 400 according to Modification 3, lamination is performed so that the alumina ceramic material 5 abuts against the first alumina layer 221 in the mixed region CM of the first composite ceramic layer 401. Accordingly, a leakage current hardly flows into the first electrode layer 241 in comparison with the reverse case (see Embodiment 3 and FIG. 12). Thus, the influence of the leakage current can be reduced.

An example using the composite ceramic green sheet CG1 according to Embodiment 1 (see FIG. 6) as the first composite ceramic layer 401 has been described in Modification 3. However, another composite ceramic green sheet, for example, the aforementioned composite ceramic green sheet CG2 or CG3 according to Modification 1 or 2, may be used. Also in this case, the stress caused by the difference in firing behavior can be reduced if the alumina ceramic material abuts against the first alumina layer 221 over a wider area than the zirconia solid-electrolyte ceramic material 6 in the portion of the mixed region CM abutting against the first alumina layer 221. In addition, it is also possible to reduce the influence of a leakage current from the heater wiring layer 261 on the gas sensor output.

Embodiment 4

Next, description will be made about a gas sensor 300 according to Embodiment 4. The gas sensor 300 according to Embodiment 4 is a gas sensor using the aforementioned gas sensor device 200 according to Embodiment 3 (see FIG. 12) or the aforementioned gas sensor device 400 according to Modification 3 (see FIG. 14).

Figure 13:
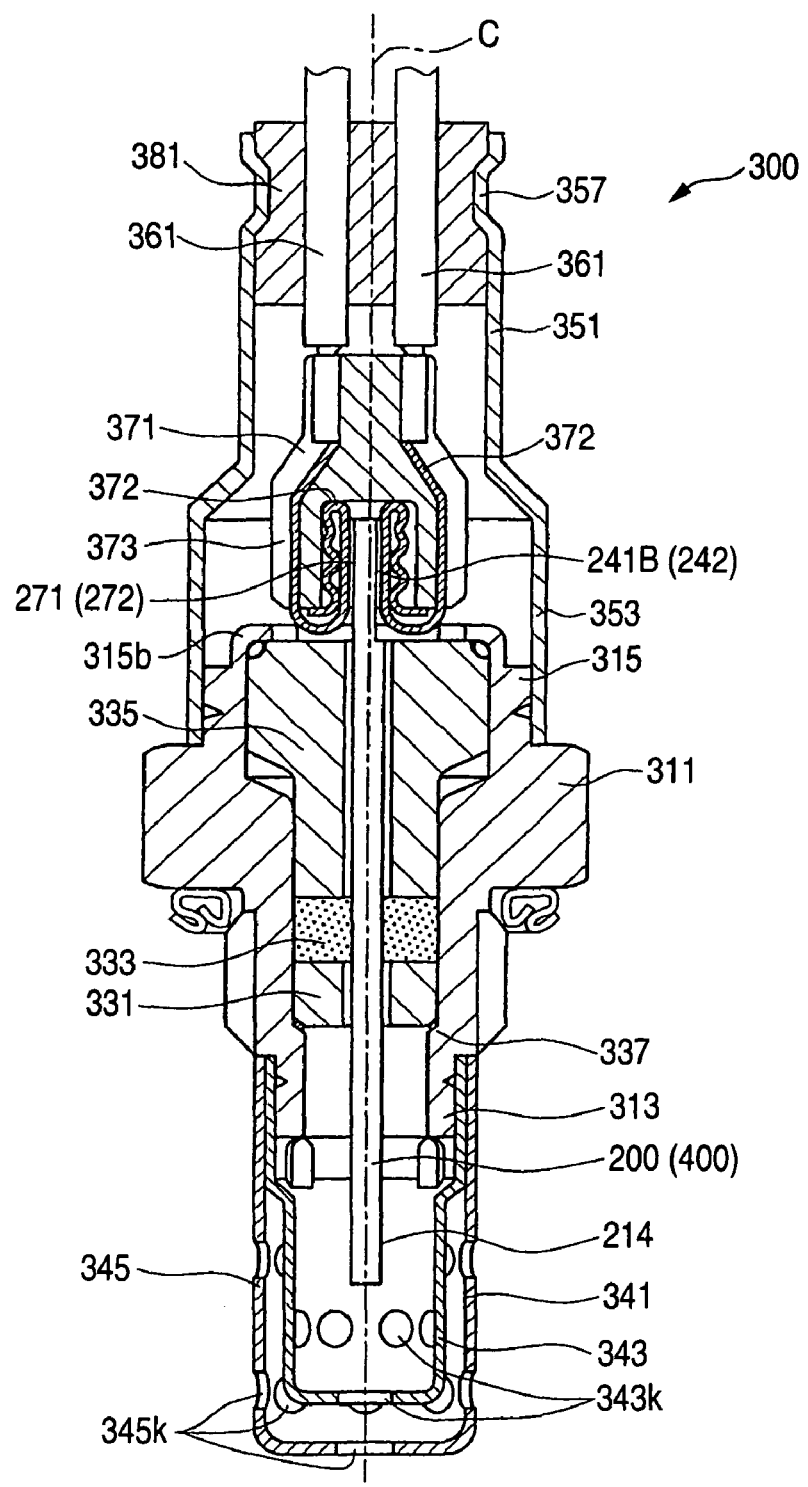
FIG. 13 is an explanatory view showing an example of a form of a gas sensor using the gas sensor device shown in FIG. 12 or 14.

The gas sensor 300 is an oxygen sensor attached to an exhaust gas pipe of an internal combustion engine and for measuring the oxygen concentration in exhaust gas. Specifically, as shown in FIG. 13, the gas sensor 300 is constituted by a gas sensor device 200 (400) extending in the axis C direction, a terminal unit 371 attached to the rear end side (upper side in FIG. 13) of the gas sensor device 200 and constituted by a ceramic separator 373 and a metal terminal 372, a metal shell 311 surrounding the gas sensor device 200, a protector 341 attached to the front end side of the metal shell 311, a metal outer casing 351 attached to the rear end side of the metal shell 311, etc.

The metal shell 311 includes a front end portion 313 having a cylindrical shape and to be inserted into the protector 341, and a rear end portion 315 to be inserted into the metal outer casing 351. Inside the metal shell 311, the gas sensor device 200 is retained axially through a packing 337, a first support member 331, a packing sealing layer 333 filled with talcum powder or the like, etc. Further, on the rear end side of the packing sealing layer 333, a cylindrical second support member 335 is disposed so that the sensor device 200 (400) can penetrate the inside of the cylindrical second support member 335. On the rear end side of the second support member 335, a thin portion on the rear end side of the rear end portion 315 of the metal shell 311 is caulked inward in the axial direction. Thus, a caulked portion 315b is formed so that the gas sensor device 200 is kept airtight inside the metal shell 311 through the first support member 331 etc.

In addition, the protector 341 has an inside cover portion 343 shaped into a closed-bottom cylinder, and an outside cover portion 345 shaped into a closed-bottom cylinder. The inside cover portion 343 covers the front end portion of the gas sensor device 200 (400), that is, the zirconia region C2 through a gap. In the inside cover portion 343, inside gas introduction holes 343K are formed. The outside cover portion 345 is disposed over the outer circumference of the inside cover portion 343. In the outside cover portion 345, outside gas introduction holes 345K are formed.

The metal outer casing 351 is shaped into a thin cylinder, covering the terminal unit 371 through a gap. A front end portion 353 of the metal outer casing 351 is circumferentially laser-welded with the rear end portion 315 of the metal shell 311 so as to be fixedly attached to the metal shell 311. A grommet 359 made of fluorocarbon rubber is fitted into the rear end of the metal outer casing 351. Four lead wires 361 are inserted into a grommet 361. When the metal outer casing 351 is caulked in the caulked portion 357, the sealing performance between the grommet 381 and the metal outer casing 351 and between the grommet 381 and each lead wire 361 can be maintained.

The terminal unit 371 is held by four metal terminals 372 in the base end portion of the gas sensor device 200 (400). The metal terminals 372 are connected to the pad portion 241B, the second electrode 242 and the pad layers 271 and 272 of the gas sensor device 200 (400) respectively.

In the gas sensor 300, the aforementioned reliable gas sensor device 200 (400) suppressing occurrence of cracks with a simple structure is used. Therefore, the gas sensor 300 is an inexpensive reliable gas sensor.

The invention has been described above along its embodiments and modifications. However, the invention is not limited to the aforementioned embodiments and so on. Not to say, the invention can be applied with suitable changes without departing from its scope and spirit.

For example, in Embodiment 1 and Modifications 1 and 2, the lip coater type sheet manufacturing apparatus 10 is used to introduce slurries to the doctor edge portion 18 (edge 19) while applying pressure to the slurries. However, any method may be used if it can apply slurries (first and second slurries 1 and 2) onto the web W. That is, using a suitable method such as a so-called doctor blade method, the first and second slurries are mixed in a mixing space before the slurries reaches the blade (edge). Thus, a composite ceramic green sheet can be manufactured.

Embodiments 2 and 3 and Modification 3 show gas sensor devices, and Embodiment 4 shows a gas sensor using a gas sensor device, by way of example. However, the gas sensor devices may be based on another form. Likewise, the gas sensor may be based on another form.

This application is based on Japanese Patent application JP 2004-54136, filed Feb. 27, 2004, and Japanese Patent application JP 2005-7860, filed Jan. 14, 2005, the entire contents of which are hereby incorporated by reference, the same as if set forth at length.

What is claimed is:

1. A method for manufacturing a composite ceramic green sheet using a sheet manufacturing apparatus, said apparatus comprising a partitioned nozzle head having a partition member which separates a first slurry from a second slurry with a predetermined space therebetween and a web disposed just above the partitioned nozzle head, the partition member having a web opposed surface that is opposed to the web while being in contact with the web or while being at a slight distance from the web, a roller disposed on an upper surface of the web and that is configured to feed the web by rotation of the roller, and a mixing space where the partition member is not present in a widthwise direction of the web formed between a front end surface of the partition member and an edge of a regulating member, said composite ceramic green sheet constituting a single sheet and having a plurality of sheet portions adjacent one another in stripe form, which method comprises:

applying, by rotation of the roller, the first slurry onto a lower surface of the web and the second slurry separated by the partition member from the first slurry onto a lower surface of said web at a distance from said first slurry in the widthwise direction, said first slurry containing a first sheet material, and said second slurry containing a second sheet material having a different sheet forming behavior from said first slurry; and expanding said first slurry on said web toward said second slurry in said widthwise direction, expanding said second slurry on said web toward said first slurry in said widthwise direction, so as to form a slurry mixed portion in said mixing space in which said first slurry and said second slurry are mixed on the web, and regulating a coating thickness of said first and second slurries with the edge of said regulating member after forming said slurry mixed portion;

wherein a first sheet portion made of said first sheet material and a second sheet portion made of said second sheet material are integrated with each other through a mixed portion provided between said first sheet portion and said second sheet portion in which said first sheet material and said second sheet material are mixed.

2. The method as claimed in claim 1,
wherein
the mixed portion has a width at least twice as large as a thickness of the composite ceramic green sheet, and
wherein
said first and second sheet portions are adjacent to each other and integrated with each other through said mixed portion.

3. The method for manufacturing a composite ceramic green sheet using a sheet manufacturing apparatus as claimed in claim 1, wherein said applying step comprises lip coating.

* * * * *